US011718759B2

(12) United States Patent
Gerard et al.

(10) Patent No.: US 11,718,759 B2
(45) Date of Patent: Aug. 8, 2023

(54) SURFACE-REACTED CALCIUM CARBONATE WITH FUNCTIONAL CATIONS

(71) Applicant: OMYA INTERNATIONAL AG, Oftringen (CH)

(72) Inventors: Daniel E. Gerard, Basel (CH); Samuel Rentsch, Spiegel bei Bern (CH); Matthias Welker, Hésingue (FR); Simon Urwyler, Bern (CH); Joachim Glaubitz, Pfaffnau (CH); Martina Elisabeth Knupfer, Rotkreuz (CH); Patrick A. C. Gane, Rothrist (CH)

(73) Assignee: Omya International AG, Oftringen (CH)

( * ) Notice: Subject to any disclaimer, the term of this patent is extended or adjusted under 35 U.S.C. 154(b) by 19 days.

(21) Appl. No.: 17/492,216

(22) Filed: Oct. 1, 2021

(65) Prior Publication Data

US 2022/0017753 A1 Jan. 20, 2022

Related U.S. Application Data

(62) Division of application No. 16/320,654, filed as application No. PCT/EP2017/068359 on Jul. 20, 2017, now Pat. No. 11,168,219.

(60) Provisional application No. 62/369,291, filed on Aug. 1, 2016.

(30) Foreign Application Priority Data

Jul. 25, 2016 (EP) ..................................... 16181085

(51) Int. Cl.
*C09C 1/02* (2006.01)
*D21H 17/67* (2006.01)
*D21H 19/38* (2006.01)
*D21H 21/52* (2006.01)

(52) U.S. Cl.
CPC ........... *C09C 1/022* (2013.01); *D21H 17/675* (2013.01); *D21H 19/385* (2013.01); *D21H 21/52* (2013.01); *C01P 2004/51* (2013.01); *C01P 2004/61* (2013.01); *C01P 2004/62* (2013.01); *C01P 2004/64* (2013.01); *C01P 2006/12* (2013.01); *C01P 2006/14* (2013.01); *C01P 2006/16* (2013.01); *C01P 2006/22* (2013.01)

(58) Field of Classification Search
CPC .. C09C 1/022; C01P 2004/51; C01P 2004/61; C01P 2004/62; C01P 2004/64; C01P 2006/12; C01P 2006/14; C01P 2006/16; C01P 2006/22; D21H 7/675
See application file for complete search history.

(56) References Cited

U.S. PATENT DOCUMENTS

| | | | |
|---|---|---|---|
| 4,167,423 A ‡ | 9/1979 | Williams ................. | C08K 9/02 106/431 |
| 7,638,017 B2 ‡ | 12/2009 | Gane ....................... | C09C 1/021 162/158 |
| 8,771,661 B2 ‡ | 7/2014 | MacDonald .......... | B01J 20/041 977/773 |
| 9,096,761 B2 ‡ | 8/2015 | Gane ....................... | C08K 9/04 |
| 9,234,102 B2 ‡ | 1/2016 | Gane ....................... | C02F 1/68 |
| 9,943,079 B2 ‡ | 4/2018 | Lu ........................... | A01N 25/08 |
| 2006/0162884 A1 ‡ | 7/2006 | Gane ..................... | D21H 19/385 162/158 |
| 2006/0246149 A1 ‡ | 11/2006 | Buchholz ................. | A61Q 1/02 424/641 |
| 2012/0186492 A1 ‡ | 7/2012 | Gane .................... | D21H 17/675 106/465 |
| 2014/0248340 A1 * | 9/2014 | Schwarzentruber .......................... | A61K 9/4816 427/2.21 |

FOREIGN PATENT DOCUMENTS

| | | | | |
|---|---|---|---|---|
| EP | 1084203 | B1 | 3/2001 | |
| EP | 1712523 | A1 | 10/2006 | |
| EP | 1712597 | A1 | 10/2006 | |
| EP | 2029675 | B1 | 3/2009 | |
| EP | 2264109 | B1 | 12/2010 | |
| EP | 2371766 | B1 | 10/2011 | |
| EP | 2421507 | A1 | 2/2012 | |
| EP | 2447213 | B1 | 5/2012 | |
| EP | 2524898 | B1 | 11/2012 | |
| EP | 2719376 | B1 | 4/2014 | |
| EP | 2921173 | A1 | 9/2015 | |
| EP | 2957603 | A1 | 12/2015 | |
| EP | 3088475 | A1 | 11/2016 | |
| EP | 3 103 844 | | * 12/2016 | ............... C09C 1/02 |
| EP | 3157583 | A1 | 4/2017 | |
| FR | 2787802 | ‡ | 6/2000 | |
| JP | 2012-524734 | A | 10/2012 | |
| WO | 99/52984 | | 10/1999 | |
| WO | 00/39222 | | 7/2000 | |
| WO | 2004/083316 | | 9/2004 | |
| WO | 2005/121257 | | 12/2005 | |

(Continued)

OTHER PUBLICATIONS

P. Papadopoulos, D.L.Rowell, "The reactions of copper and zinc with calcium carbonate surfaces", Journal of Soil Science, Mar. 1989, vol. 40, pp. 39-48.‡

(Continued)

*Primary Examiner* — Pegah Parvini
(74) *Attorney, Agent, or Firm* — Heslin Rothenberg Farley & Mesiti, PC

(57) ABSTRACT

A surface-reacted calcium carbonate is described. In embodiments, the surface-reacted calcium carbonate is obtained by a process comprising treating a calcium carbonate-comprising material with at least one $H_3O^+$ ion donor, carbon dioxide, and at least one water-soluble metal cation source in an aqueous medium to form an aqueous suspension of surface-reacted calcium carbonate.

24 Claims, No Drawings

(56) References Cited

FOREIGN PATENT DOCUMENTS

| WO | 2014/128087    | 12/2007 |
| WO | 2009/074492    | 6/2009  |
| WO | 2010/121619 A1 | 10/2010 |
| WO | 2010/146530    | 12/2010 |
| WO | 2010/146531    | 12/2010 |
| WO | 2013/142473    | 9/2013  |
| WO | 2007/141260    | 4/2014  |
| WO | 2015/193299 A1 | 12/2015 |

OTHER PUBLICATIONS

Japanese Office Action dated Apr. 6, 2021 in corresponding Japanese Patent Application No. 2019-503675 and English translation.‡
International Search Report and Written Opinion dated Aug. 9, 2017 in corresponding International Patent Application No. PCT/EP2017/068359, filed Jul. 20, 2017, 12 pages.‡

\* cited by examiner
‡ imported from a related application

SURFACE-REACTED CALCIUM CARBONATE WITH FUNCTIONAL CATIONS

CROSS-REFERENCE TO PRIOR APPLICATIONS

This application is a Divisional of U.S. application Ser. No. 16/320,654, filed Jan. 25, 2019 which is a National Stage of PCT/EP2017/068359, filed Jul. 20, 2017, and designating the United States (published on Feb. 1, 2018, as WO 2018/019699 A1), which claims priority under 35 U.S.C. § 119 to European Patent Application No. 16181085.8, filed Jul. 25, 2016, and under 35 U.S.C. § 120 to Provisional Application No. 62/369,291, filed Aug. 1, 2016, each hereby expressly incorporated by reference in its entirety and each assigned to the assignee hereof.

The present invention relates to a surface-reacted calcium carbonate, a process for manufacturing the same, and its use.

In the year of 1998, a new type of surface-reacted calcium carbonate was first described in FR 2787802 B1, subsequently in WO 00/39222 A1 and US 2004/0020410 A1, and is based on the reaction of natural ground calcium carbonate with gaseous $CO_2$ and with one or more medium-strong to strong $H_3O^+$ ion providers. The obtained product is a porous calcium carbonate having a special surface structure, porosity, and specific surface area providing a reduction in the weight of paper for a constant surface area without loss of physical properties, when it is used as a pigment or coating filler for the said paper.

In WO 2004/083316 A1, a further advantageous modification in the preparation of this surface-reacted calcium carbonate is described, wherein aluminium silicate, synthetic silica, calcium silicate, silicates and/or monovalent salt are involved, and which are also useful in paper-making applications.

Also, WO 2005/121257 A2 refers to the addition of advantageous additives in the production of said surface-reacted calcium carbonate, wherein one or more compounds of formula R-X are added, which, e.g. are selected from fatty acids, fatty amines or fatty alcohols.

WO 2009/074492 A1 especially relates to the optimization of the known process as regards precipitated calcium carbonate, as it turned out that due to the special conditions in the precipitation of calcium carbonate, the process useful for natural ground calcium carbonate did not provide the same good results for the surface-reaction of synthetic precipitated calcium carbonate.

Several further optimizations and modifications of the process for the preparation of surface-reacted calcium carbonate followed such as those described in WO 2010/146530 A1 and WO 2010/146531 A1 involving the use of weak acids in the preparation of surface-reacted calcium carbonate.

EP 2 957 603 A1 describes a method for producing granules comprising surface-reacted calcium carbonate.

The characteristics of these particulate materials may be further improved or modified by additional surface-treatments, for example, in order to improve hydrophobicity/hydrophilicity or acid-resistance. Another aim is to locate surface-treatment agents on the surface of these particulate materials in order to use them as carrier material.

For example, EP 1 084 203 refers to composite compositions comprising at least two mineral or organic fillers or pigments and at least one binding agent. The mineral or organic fillers or pigments have undergone a physical or chemical treatment such that they have at least one organophilic site.

EP 2 029 675 refers to composites of inorganic and/or organic microparticles and nano-calcium carbonate particles. The surface of these particulate materials is coated with the help of binders.

US 2012/0202684 relates to high surface area materials, such as nanoparticles, which are coated with metal ions by absorbing the metal ions on the surface of the nanoparticles. The obtained modified particles can be used for removing gaseous compounds or for neutralizing odour.

However, there is still a need in the art for methods for producing surface-reacted calcium carbonate, and, in particular, modified surface-reacted calcium carbonate, which provides additional functionalities.

Aqueous preparations, for example, and especially suspensions, dispersions or slurries of minerals, fillers or pigments, which are used extensively in the paper, paint, rubber and plastics industries as coatings, fillers, extenders and pigments for papermaking as well as aqueous lacquers and paints are often subject to microbial contamination. Such a contamination can result in changes in the preparation properties such as changes in viscosity and/or pH, discolorations or reductions in other quality parameters, which negatively affect their commercial value. The contaminated filler aqueous preparations may also transmit the microorganisms to the later produced product, for example, the plastic or paper product. Therefore, for ensuring an acceptable microbiological quality of aqueous preparations, preservatives or biocides are used over the entire life cycle of the preparation (production, storage, transport, use).

Preservatives are also typically added to pharmaceutical, cosmetic or food products to prevent decomposition by microbial growth or by undesirable chemical changes and to avoid any health hazards. However, many of these preservatives are themselves subject to health concerns, and thus, are increasingly rejected by consumers.

Dry film preservation, meaning preservation of dry products such as coatings and building materials from microbiological degradation to avoid material destruction and visible disfigurement, is also an important and difficult challenge. Preservatives for dry film preservation are typically incorporated in the product and preserve the dry product over a longer period of time by an antimicrobial activity on the dry or wet surface. Such an antimicrobial surface activity is of advantage not only to protect the product itself from degradation or defacement but also to avoid contamination of a surface with pathogenic microorganisms. This is particular useful in the health care sector. However, there is the risk that preservatives are eluted from the dry product over time, for example, due to rain or humid environment, which may pose a danger to human health and the environment.

US 2006/0246149 A1 describes antimicrobial pigments, which are obtainable by agitating a suspension comprising one or more pigments and silver oxide as antimicrobial compound. A modified mineral-based filler with enhanced retention of at least one active ingredient or enhanced antimicrobial capabilities is disclosed in US 2010/0260866. A study concerning copper precipitation from sulphate solutions with calcium carbonate was published by Zhizhaev et al. (Russian Journal of Applied Chemistry 2007, 80(10), 1632-1635).

However, there is still a need in the art for harmless materials with antimicrobial activity, which are suitable for a wide range of applications.

Accordingly, it is an object of the present invention to provide a process for producing a surface-reacted calcium carbonate which provides further functionalities. It is desirable that the obtained surface-reacted calcium carbonate can be used as filler material so that it may replace conventionally used fillers in various applications or supplement them.

It is also an object of the present invention to provide a material, which is at least partially derivable from natural sources and is not persistent in the environment, but easily biodegradable. It would also be desirable that said material is water-resistant, and thus, can be used in application subjected to regular water washings. It is also desirable that the functionality of the surface-reacted calcium carbonate can be controlled and can be tailored for a specific application.

It is also an object of the present invention to provide a material which can control microbial contamination but does not represent a hazard to health. It is a further object of the present invention to provide a material which, besides the antimicrobial activity, has additional benefits. For example, it would be desirable that such a material confers or enhances the antimicrobial activity of a product, in which it is incorporated, over an extended period without affecting the properties of the product in a negative way. It would also be desirable to provide a material that is suitable for agricultural applications and can release micronutrients to plants.

The foregoing and other objects are solved by the subject-matter as defined in the independent claims.

According to one aspect of the present invention, a process for producing a surface-reacted calcium carbonate is provided, the process comprising the steps of:
 a) providing a calcium carbonate-comprising material,
 b) providing at least one $H_3O^+$ ion donor,
 c) providing at least one water-soluble metal cation source, and
 d) treating the calcium carbonate-comprising material of step a) with the at least one $H_3O^+$ ion donor of step b) and carbon dioxide in an aqueous medium to form an aqueous suspension of surface-reacted calcium carbonate,
 wherein the carbon dioxide is formed in-situ by the $H_3O^+$ ion donor treatment and/or is supplied from an external source, and
 wherein the at least one water-soluble metal cation source of step c) is added during step d).

According to a further aspect, a surface-reacted calcium carbonate obtainable by a process according to the present invention is provided.

According to still a further aspect, a composition comprising a surface-reacted calcium carbonate according to the present invention is provided, preferably further comprising an additional surface-reacted calcium carbonate, wherein the additional surface-reacted calcium carbonate is a reaction product of natural ground calcium carbonate or precipitated calcium carbonate with carbon dioxide and at least one $H_3O^+$ ion donor, wherein the carbon dioxide is formed in-situ by the $H_3O^+$ ion donor treatment and/or is supplied from an external source.

According to still a further aspect, a use of a surface-reacted calcium carbonate according to the present invention or a composition according to the present invention as preservative, for the control of odour, and/or for enhancing and/or mediating antimicrobial activity of a substrate is provided.

According to still a further aspect, a use of a surface-reacted calcium carbonate according to the present invention or a composition according to the present invention as a metal cation releaser, preferably as micronutrient delivery agent and/or plant protection product is provided.

According to still a further aspect, a use of a surface-reacted calcium carbonate according to the present invention or a composition according to the present invention for enhancing the electrical conductivity of a substrate is provided.

According to still a further aspect, use of a surface-reacted calcium carbonate according to the present invention or a composition according to the present invention in polymer applications, paper coating applications, paper making, paints, coatings, sealants, printing inks, adhesives, food, feed, pharmaceuticals, concrete, cement, cosmetics, water treatment, engineered wood applications, plasterboard applications, packaging applications and/or agricultural applications is provided.

According to still a further aspect, an article comprising a surface-reacted calcium carbonate according to the present invention or a composition according to the present invention is provided, wherein the article is selected from paper products, engineered wood products, plasterboard products, polymer products, hygiene products, medical products, healthcare products, filter products, woven materials, non-woven materials, geotextile products, agricultural products, horticultural products, clothing, footwear products, baggage products, household products, industrial products, packaging products, building products, and construction products.

Advantageous embodiments of the present invention are defined in the corresponding subclaims.

According to one embodiment the calcium carbonate-comprising material is a natural ground calcium carbonate and/or a precipitated calcium carbonate, preferably the natural ground calcium carbonate is selected from the group consisting of marble, chalk, dolomite, limestone, and mixtures thereof, and/or the precipitated calcium carbonate is selected from the group consisting of precipitated calcium carbonates having an aragonitic, vateritic or calcitic crystal form, and mixtures thereof. According to a further embodiment the calcium carbonate-comprising material is in form of particles having a weight median particle size $d_{50}(wt)$ from 0.05 to 10 µm, preferably from 0.2 to 5.0 µm, more preferably from 0.4 to 3.0 µm, and most preferably from 0.6 to 1.2 µm, and/or a weight top cut particle size $d_{98}(wt)$ from 0.15 to 55 µm, preferably from 1 to 40 µm, more preferably from 2 to 25 µm, and most preferably from 3 to 15 µm.

According to one embodiment the at least one $H_3O^+$ ion donor is selected from the group consisting of hydrochloric acid, sulphuric acid, sulphurous acid, phosphoric acid, citric acid, oxalic acid, an acidic salt, acetic acid, formic acid, and mixtures thereof, preferably the at least one $H_3O^+$ ion donor is selected from the group consisting of hydrochloric acid, sulphuric acid, sulphurous acid, phosphoric acid, oxalic acid, $H_2PO_4^-$, being at least partially neutralised by a cation selected from $Li^+$, $Na^+$ and/or $K^+$, $HPO_4^{2-}$, being at least partially neutralised by a cation selected from $Li^+$, $Na^+$, $Mg^{2+}$, and/or $Ca^{2+}$, and mixtures thereof, more preferably the at least one $H_3O^+$ ion donor is selected from the group consisting of hydrochloric acid, sulphuric acid, sulphurous acid, phosphoric acid, oxalic acid, or mixtures thereof, and most preferably, the at least one $H_3O^+$ ion donor is phosphoric acid. According to a further embodiment the molar ratio of the at least one $H_3O^+$ ion donor to the calcium carbonate-comprising material is from 0.01 to 4, preferably from 0.02 to 2, more preferably from 0.05 to 1, and most preferably from 0.1 to 0.58.

According to one embodiment the at least one water-soluble metal cation source is selected from the group consisting of a water-soluble metal salt, a water-soluble transition metal complex, a water-soluble metal hydroxide, a water-soluble metal oxide, and mixtures thereof, preferably the water-soluble metal cation source is selected from the group consisting of a water-soluble transition metal salt, a water-soluble group(III) metal salt, and mixtures thereof, more preferably the water-soluble metal cation source is selected from the group consisting of water-soluble salts of aluminium, chromium, manganese, iron, cobalt, nickel, copper, zinc, silver, gold, zirconium, platinum, palladium, and mixtures thereof, and most preferably the water-soluble metal cation source is selected from the group consisting of copper nitrate, copper sulphate, copper acetate, copper chloride, copper bromide, copper iodide, zinc nitrate, zinc sulphate, zinc acetate, zinc chloride, zinc bromide, zinc iodide, hydrates thereof, and mixtures thereof. According to a further embodiment the at least one water-soluble metal cation source is provided in an amount from 0.01 to 60 wt. %, based on the total weight of the calcium carbonate-comprising material, preferably from 0.05 to 50 wt. %, more preferably from 0.1 to 25 wt. %, and most preferably from 0.5 to 10 wt. %.

According to one embodiment in step d) the calcium carbonate-comprising material is treated with a solution comprising the at least one $H_3O^+$ ion donor of step b) and the at least one water-soluble metal cation source of step c). According to a further embodiment in step d) the calcium carbonate-comprising material is treated with a first solution comprising a first part of the at least one $H_3O^+$ ion donor of step b), and subsequently, with a second solution comprising the remaining part of the at least one $H_3O^+$ ion donor of step b) and the at least one water-soluble metal cation source of step c). According to still a further embodiment step d) is carried out at a temperature from 20 to 90° C., preferably from 30 to 85° C., more preferably from 40 to 80° C., even more preferably from 50 to 75° C., and most preferably from 60 to 70° C.

According to one embodiment the process further comprises a step e) of separating the surface-reacted calcium carbonate from the aqueous suspension obtained in step d). According to a further embodiment the process further comprises a step f) of drying the surface-reacted calcium carbonate after step d) or after step e), if present, at a temperature in the range from 60 to 600° C., preferably until the moisture content of the surface-reacted calcium carbonate is between 0.01 and 5 wt. %, based on the total weight of the dried surface-reacted calcium carbonate.

According to one embodiment the calcium carbonate-comprising material is a natural ground calcium carbonate, the at least one $H_3O^+$ ion donor is phosphoric acid, the at least one water-soluble metal cation source is selected from the group consisting of copper nitrate, copper sulphate, copper acetate, copper chloride, copper bromide, copper iodide, zinc nitrate, zinc sulphate, zinc acetate, zinc chloride, zinc bromide, zinc iodide, hydrates thereof, and mixtures thereof, and in step d) the calcium carbonate-comprising material is treated with a solution comprising the at least one $H_3O^+$ ion donor of step b) and the at least one water-soluble metal cation source of step c).

According to one embodiment the surface-reacted calcium carbonate has a specific surface area of from 15 m²/g to 200 m²/g, preferably from 20 m²/g to 180 m²/g, more preferably from 25 m²/g to 160 m²/g, even more preferably from 27 m²/g to 150 m²/g, most preferably from 30 m²/g to 140 m²/g, measured using nitrogen and the BET method. According to a further embodiment the surface-reacted calcium carbonate has a volume determined median particle size $d_{50}(vol)$ from 1 to 75 μm, preferably from 2 to 50 μm, more preferably from 3 to 40 μm, even more preferably from 4 to 30 μm, and most preferably from 5 to 15 μm, and/or a volume determined top cut particle size $d_{98}(vol)$ from 2 to 150 μm, preferably from 4 to 100 μm, more preferably from 6 to 80 μm, even more preferably from 8 to 60 μm, and most preferably from 10 to 30 μm.

According to one embodiment the surface-reacted calcium carbonate has an intra-particle intruded specific pore volume in the range from 0.1 to 2.3 cm³/g, preferably from 0.2 to 2.0 cm³/g, more preferably from 0.4 to 1.8 cm³/g, and most preferably from 0.6 to 1.6 cm³/g, calculated from mercury porosimetry measurement. According to a further embodiment the surface-reacted calcium carbonate has an intra-particle pore size in a range of from 0.004 to 1.6 μm, preferably in a range of between 0.005 to 1.3 μm, more preferably from 0.006 to 1.15 μm, and most preferably of 0.007 to 1.0 μm, determined from mercury porosity measurement.

It should be understood that for the purpose of the present invention, the following terms have the following meaning:

A "calcium carbonate-comprising material" in the meaning of the present invention can be a mineral material or a synthetic material having a content of calcium carbonate of at least 50 wt. %, preferably 75 wt. %, more preferably 90 wt. %, and most preferably 95 wt. %, based on the total weight of the calcium carbonate-comprising material.

For the purpose of the present application, "water-insoluble" materials are defined as materials which, when 100 g of said material is mixed with 100 g deionised water and filtered on a filter having a 0.2 μm pore size at 20° C. to recover the liquid filtrate, provide less than or equal to 1 g of recovered solid material following evaporation at 95 to 100° C. of 100 g of said liquid filtrate at ambient pressure. "Water-soluble" materials are defined as materials which, when 100 g of said material is mixed with 100 g deionised water and filtered on a filter having a 0.2 μm pore size at 20° C. to recover the liquid filtrate, provide more than 1 g of recovered solid material following evaporation at 95 to 100° C. of 100 g of said liquid filtrate at ambient pressure.

"Natural ground calcium carbonate" (GCC) in the meaning of the present invention is a calcium carbonate obtained from natural sources, such as limestone, marble, or chalk, and processed through a wet and/or dry treatment such as grinding, screening and/or fractionating, for example, by a cyclone or classifier.

"Precipitated calcium carbonate" (PCC) in the meaning of the present invention is a synthesised material, obtained by precipitation following reaction of carbon dioxide and lime in an aqueous, semi-dry or humid environment or by precipitation of a calcium and carbonate ion source in water. PCC may be in the vateritic, calcitic or aragonitic crystal form. PCCs are described, for example, in EP 2 447 213 A1, EP 2 524 898 A1, EP 2 371 766 A1, EP 1 712 597 A1, EP 1 712 523 A1, or WO 2013/142473 A1.

The term "surface-reacted" in the meaning of the present application shall be used to indicate that a material has been subjected to a process comprising partial dissolution of said material upon acidic treatment (e.g., by use of water-soluble free acids and/or acidic salts) in aqueous environment followed by a crystallization process which may occur in the absence or presence of further crystallization additives. The term "acid" as used herein refers to an acid in the meaning of the definition by Brønsted and Lowry (e.g., $H_2SO_4$, $HSO_4^-$), wherein the term "free acid" refers only to those acids being in the fully protonated form (e.g., $H_2SO_4$).

The "particle size" of particulate materials other than surface-reacted calcium carbonate herein is described by its distribution of particle sizes $d_x$. Therein, the value $d_x$ represents the diameter relative to which x % by weight of the particles have diameters less than $d_x$. This means that, for example, the $d_{20}$ value is the particle size at which 20 wt. % of all particles are smaller than that particle size. The $d_{50}$ value is thus the weight median particle size, i.e. 50 wt. % of all particles are smaller than this particle size. For the purpose of the present invention, the particle size is specified as weight median particle size $d_{50}$(wt.) unless indicated otherwise. Particle sizes were determined by using a Sedigraph™ 5100 instrument or Sedigraph™ 5120 instrument of Micromeritics Instrument Corporation. The method and the instrument are known to the skilled person and are commonly used to determine the particle size of fillers and pigments. The measurements were carried out in an aqueous solution of 0.1 wt. % $Na_4P_2O_7$.

The "particle size" of surface-reacted calcium carbonate herein is described as volume-based particle size distribution. Volume-based median particle size $d_{50}$ was evaluated using a Malvern Mastersizer 2000 Laser Diffraction System. The $d_{50}$ or $d_{98}$ value, measured using a Malvern Mastersizer 2000 Laser Diffraction System, indicates a diameter value such that 50% or 98% by volume, respectively, of the particles have a diameter of less than this value. The raw data obtained by the measurement are analysed using the Mie theory, with a particle refractive index of 1.57 and an absorption index of 0.005.

The "specific surface area" (expressed in $m^2/g$) of a material as used throughout the present document can be determined by the Brunauer Emmett Teller (BET) method with nitrogen as adsorbing gas and by use of a ASAP 2460 instrument from Micromeritics. The method is well known to the skilled person and defined in ISO 9277:2010. Samples are conditioned at 100° C. under vacuum for a period of 30 min prior to measurement. The total surface area (in $m^2$) of said material can be obtained by multiplication of the specific surface area (in $m^2/g$) and the mass (in g) of the material.

In the context of the present invention, the term "pore" is to be understood as describing the space that is found between and/or within particles, i.e. that is formed by the particles as they pack together under nearest neighbour contact (interparticle pores), such as in a powder or a compact and/or the void space within porous particles (intraparticle pores), and that allows the passage of liquids under pressure when saturated by the liquid and/or supports absorption of surface wetting liquids.

The specific pore volume is measured using a mercury intrusion porosimetry measurement using a Micromeritics Autopore V 9620 mercury porosimeter having a maximum applied pressure of mercury 414 MPa (60 000 psi), equivalent to a Laplace throat diameter of 0.004 μm (~nm). The equilibration time used at each pressure step is 20 seconds. The sample material is sealed in a 3 $cm^3$ chamber powder penetrometer for analysis. The data are corrected for mercury compression, penetrometer expansion and sample material compression using the software Pore-Comp (Gane, P. A. C., Kettle, J. P., Matthews, G. P. and Ridgway, C. J., "Void Space Structure of Compressible Polymer Spheres and Consolidated Calcium Carbonate Paper-Coating Formulations", Industrial and Engineering Chemistry Research, 35(5), 1996, p 1753-1764.).

The total pore volume seen in the cumulative intrusion data can be separated into two regions with the intrusion data from 214 μm down to about 1-4 μm showing the coarse packing of the sample between any agglomerate structures contributing strongly. Below these diameters lies the fine interparticle packing of the particles themselves. If they also have intraparticle pores, then this region appears bi modal, and by taking the specific pore volume intruded by mercury into pores finer than the modal turning point, i.e. finer than the bi-modal point of inflection, we thus define the specific intraparticle pore volume. The sum of these three regions gives the total overall pore volume of the powder, but depends strongly on the original sample compaction/settling of the powder at the coarse pore end of the distribution.

By taking the first derivative of the cumulative intrusion curve the pore size distributions based on equivalent Laplace diameter, inevitably including pore-shielding, are revealed. The differential curves clearly show the coarse agglomerate pore structure region, the interparticle pore region and the intraparticle pore region, if present. Knowing the intraparticle pore diameter range it is possible to subtract the remainder interparticle and interagglomerate pore volume from the total pore volume to deliver the desired pore volume of the internal pores alone in terms of the pore volume per unit mass (specific pore volume). The same principle of subtraction, of course, applies for isolating any of the other pore size regions of interest.

For the purpose of the present invention, the "solids content" of a liquid composition is a measure of the amount of material remaining after all the solvent or water has been evaporated. If necessary, the "solids content" of a suspension given in wt. % in the meaning of the present invention can be determined using a Moisture Analyzer HR73 from Mettler-Toledo (T=120° C., automatic switch off 3, standard drying) with a sample size of 5 to 20 g.

Unless specified otherwise, the term "drying" refers to a process according to which at least a portion of water is removed from a material to be dried such that a constant weight of the obtained "dried" material at 120° C. is reached. Moreover, a "dried" or "dry" material may be defined by its total moisture content which, unless specified otherwise, is less than or equal to 1.0 wt. %, preferably less than or equal to 0.5 wt. %, more preferably less than or equal to 0.2 wt. %, and most preferably between 0.03 and 0.07 wt. %, based on the total weight of the dried material.

For the purpose of the present invention, the term "viscosity" or "Brookfield viscosity" refers to Brookfield viscosity. The Brookfield viscosity is for this purpose measured by a Brookfield DV-II+ Pro viscometer at 25° C.±1° C. at 100 rpm using an appropriate spindle of the Brookfield RV-spindle set and is specified in mPa·s. Based on his technical knowledge, the skilled person will select a spindle from the Brookfield RV-spindle set which is suitable for the viscosity range to be measured. For example, for a viscosity range between 200 and 800 mPa·s the spindle number 3 may be used, for a viscosity range between 400 and 1 600 mPa·s the spindle number 4 may be used, for a viscosity range between 800 and 3 200 mPa·s the spindle number 5 may be used, for a viscosity range between 1 000 and 2 000 000 mPa·s the spindle number 6 may be used, and for a viscosity range between 4 000 and 8 000 000 mPa·s the spindle number 7 may be used.

A "suspension" or "slurry" in the meaning of the present invention comprises undissolved solids and water, and optionally further additives, and usually contains large amounts of solids and, thus, is more viscous and can be of higher density than the liquid from which it is formed.

Where an indefinite or definite article is used when referring to a singular noun, e.g., "a", "an" or "the", this includes a plural of that noun unless anything else is specifically stated.

Where the term "comprising" is used in the present description and claims, it does not exclude other elements.

For the purposes of the present invention, the term "consisting of" is considered to be a preferred embodiment of the term "comprising". If hereinafter a group is defined to comprise at least a certain number of embodiments, this is also to be understood to disclose a group, which preferably consists only of these embodiments.

Terms like "obtainable" or "definable" and "obtained" or "defined" are used interchangeably. This, for example, means that, unless the context clearly dictates otherwise, the term "obtained" does not mean to indicate that, for example, an embodiment must be obtained by, for example, the sequence of steps following the term "obtained" though such a limited understanding is always included by the terms "obtained" or "defined" as a preferred embodiment.

Whenever the terms "including" or "having" are used, these terms are meant to be equivalent to "comprising" as defined hereinabove.

The inventive process for producing a surface-reacted calcium carbonate comprises the steps of a) providing a calcium carbonate-comprising material, b) providing at least one $H_3O^+$ ion donor, c) providing at least one water-soluble metal cation source, and d) treating the calcium carbonate-comprising material of step a) with the at least one $H_3O^+$ ion donor of step b) and carbon dioxide in an aqueous medium to form an aqueous suspension of surface-reacted calcium carbonate. The carbon dioxide is formed in-situ by the $H_3O^+$ ion donor treatment and/or is supplied from an external source. The at least one water-soluble metal cation source of step c) is added during step d).

In the following preferred embodiments of the inventive composition will be set out in more detail. It is to be understood that these embodiments and details also apply to the inventive products and uses.

Process Step a)

According to step a) of the process of the present invention, a calcium-carbonate comprising material is provided.

According to one embodiment the at least one calcium carbonate-comprising material has a content of calcium carbonate of at least 50 wt. %, preferably 75 wt. %, more preferably 90 wt. %, and most preferably 95 wt. %, based on the total weight of the calcium carbonate-comprising material. According to another embodiment the at least one calcium carbonate comprising material consists of calcium carbonate.

The calcium carbonate-comprising material may be selected from natural ground calcium carbonate, precipitated calcium carbonate, dolomite, or mixtures thereof. The natural ground calcium carbonate may be preferably selected from marble, limestone and/or chalk, and/or the precipitated calcium carbonate may be preferably selected from vaterite, calcite and/or aragonite According to one embodiment of the present invention, the calcium carbonate-comprising material is a natural ground calcium carbonate and/or a precipitated calcium carbonate, preferably the natural ground calcium carbonate is selected from the group consisting of marble, chalk, dolomite, limestone, and mixtures thereof, and/or the precipitated calcium carbonate is selected from the group consisting of precipitated calcium carbonates having an aragonitic, vateritic or calcitic crystal form, and mixtures thereof.

"Natural ground calcium carbonate" (GCC) is understood to be manufactured from a naturally occurring form of calcium carbonate, mined from sedimentary rocks such as limestone or chalk, or from metamorphic marble rocks, eggshells or seashells. Calcium carbonate is known to exist as three types of crystal polymorphs: calcite, aragonite and vaterite. Calcite, the most common crystal polymorph, is considered to be the most stable crystal form of calcium carbonate. Less common is aragonite, which has a discrete or clustered needle orthorhombic crystal structure. Vaterite is the rarest calcium carbonate polymorph and is generally unstable. Ground calcium carbonate is almost exclusively of the calcitic polymorph, which is said to be trigonal-rhombohedral and represents the most stable form of the calcium carbonate polymorphs. The term "source" of the calcium carbonate in the meaning of the present application refers to the naturally occurring mineral material from which the calcium carbonate is obtained. The source of the calcium carbonate may comprise further naturally occurring components such as magnesium carbonate, alumino silicate etc.

In general, the grinding of natural ground calcium carbonate may be a dry or wet grinding step and may be carried out with any conventional grinding device, for example, under conditions such that comminution predominantly results from impacts with a secondary body, i.e. in one or more of: a ball mill, a rod mill, a vibrating mill, a roll crusher, a centrifugal impact mill, a vertical bead mill, an attrition mill, a pin mill, a hammer mill, a pulveriser, a shredder, a de-clumper, a knife cutter, or other such equipment known to the skilled man. In case the calcium carbonate containing mineral material comprises a wet ground calcium carbonate containing mineral material, the grinding step may be performed under conditions such that autogenous grinding takes place and/or by horizontal ball milling, and/or other such processes known to the skilled man. The wet processed ground calcium carbonate containing mineral material thus obtained may be washed and dewatered by well-known processes, e.g. by flocculation, filtration or forced evaporation prior to drying. The subsequent step of drying (if necessary) may be carried out in a single step such as spray drying, or in at least two steps. It is also common that such a mineral material undergoes a beneficiation step (such as a flotation, bleaching or magnetic separation step) to remove impurities.

According to one embodiment of the present invention the source of natural ground calcium carbonate (GCC) is selected from marble, chalk, limestone, or mixtures thereof. Preferably, the source of ground calcium carbonate is marble, and more preferably dolomitic marble and/or magnesitic marble. According to one embodiment of the present invention the GCC is obtained by dry grinding. According to another embodiment of the present invention the GCC is obtained by wet grinding and subsequent drying.

According to one embodiment of the present invention, the calcium carbonate comprises one type of natural ground calcium carbonate. According to another embodiment of the present invention, the calcium carbonate comprises a mixture of two or more types of natural ground calcium carbonates selected from different sources.

"Precipitated calcium carbonate" (PCC) in the meaning of the present invention is a synthesized material, generally obtained by precipitation following reaction of carbon dioxide and calcium hydroxide in an aqueous environment or by precipitation of calcium and carbonate ions, for example $CaCl_2$ and $Na_2CO_3$, out of solution. Further possible ways of producing PCC are the lime soda process, or the Solvay process in which PCC is a by-product of ammonia production. Precipitated calcium carbonate exists in three primary crystalline forms: calcite, aragonite and vaterite, and there are many different polymorphs (crystal habits) for each of these crystalline forms. Calcite has a trigonal structure with typical crystal habits such as scalenohedral (S-PCC), rhombohedral (R-PCC), hexagonal prismatic, pinacoidal, colloidal (C-PCC), cubic, and prismatic (P-PCC). Aragonite is an orthorhombic structure with typical crystal habits of twinned hexagonal prismatic crystals, as well as a diverse assortment of thin elongated prismatic, curved bladed, steep pyramidal, chisel shaped crystals, branching tree, and coral or worm-like form. Vaterite belongs to the hexagonal crystal system. The obtained PCC slurry can be mechanically dewatered and dried.

According to one embodiment of the present invention, the precipitated calcium carbonate is precipitated calcium carbonate, preferably comprising aragonitic, vateritic or calcitic mineralogical crystal forms or mixtures thereof.

Precipitated calcium carbonate may be ground prior to the treatment with carbon dioxide and at least one $H_3O^+$ ion donor by the same means as used for grinding natural ground calcium carbonate as described above.

"Dolomite" in the meaning of the present invention is a calcium carbonate containing mineral, namely a carbonic calcium-magnesium-mineral, having the chemical composition of $CaMg(CO_3)_2$ ("$CaCO_3 \cdot MgCO_3$"). A dolomite mineral may contain at least 30.0 wt. % $MgCO_3$, based on the total weight of dolomite, preferably more than 35.0 wt. %, and more preferably more than 40.0 wt. % $MgCO_3$.

According to one embodiment of the present invention, the calcium carbonate-comprising material is in form of particles having a weight median particle size $d_{50}$ of 0.05 to 10.0 µm, preferably 0.2 to 5.0 µm, more preferably 0.4 to 3.0 µm, and most preferably 0.6 to 1.2 µm.

According to a further embodiment of the present invention, the calcium carbonate-comprising material is in form of particles having a top cut particle size $d_{98}$ of 0.15 to 55 µm, preferably 1 to 40 µm, more preferably 2 to 25 µm, and most preferably 3 to 15 µm.

The calcium carbonate-comprising material may have a specific surface area (BET) from 1 to 200 m$^2$/g, as measured using nitrogen and the BET method according to ISO 9277. According to one embodiment the specific surface area (BET) of the calcium carbonate-comprising material is from 1 to 150 m$^2$/g, preferably from 2 to 60 m$^2$/g, and more preferably from 2 to 15 m$^2$/g, as measured using nitrogen and the BET method according to ISO 9277.

The calcium carbonate-comprising material may be used dry or in form of an aqueous suspension. According to a preferred embodiment, the calcium carbonate-comprising material is in form of an aqueous suspension having a solids content within the range of 1 wt. % to 90 wt. %, preferably 3 wt. % to 60 wt. %, more preferably 5 wt. % to 40 wt. %, and most preferably 10 wt. % to 25 wt. %, based on the weight of the aqueous suspension.

The term "aqueous" suspension refers to a system, wherein the liquid phase comprises, preferably consists of, water. However, said term does not exclude that the liquid phase of the aqueous suspension comprises minor amounts of at least one water-miscible organic solvent selected from the group comprising methanol, ethanol, acetone, acetonitrile, tetrahydrofuran and mixtures thereof. If the aqueous suspension comprises at least one water-miscible organic solvent, the liquid phase of the aqueous suspension comprises the at least one water-miscible organic solvent in an amount of from 0.1 to 40.0 wt. % preferably from 0.1 to 30.0 wt. %, more preferably from 0.1 to 20.0 wt. % and most preferably from 0.1 to 10.0 wt. %, based on the total weight of the liquid phase of the aqueous suspension. For example, the liquid phase of the aqueous suspension consists of water.

According to a preferred embodiment of the present invention, the aqueous suspension consists of water and the calcium carbonate-comprising material.

Alternatively, the aqueous suspension of the calcium carbonate-comprising material may comprise further additives, for example, a dispersant. A suitable dispersant may be selected from polyphosphates, and is in particular a tripolyphosphate. Another suitable dispersant may be selected from the group comprising homopolymers or copolymers of polycarboxylic acid salts based on, for example, acrylic acid, methacrylic acid, maleic acid, fumaric acid or itaconic acid and acrylamide or mixtures thereof. Homopolymers or copolymers of acrylic acid are especially preferred. The weight average molecular weight $M_w$ of such products is preferably in the range from 2 000 to 15 000 g/mol, with a weight average molecular weight $M_w$ from 3 000 to 7 000 g/mol or 3 500 to 6 000 g/mol being especially preferred. According to an exemplary embodiment, the dispersant is sodium polyacrylate having a weight average molecular weight $M_w$ from 2 000 to 15 000 g/mol, preferably from 3 000 to 7 000 g/mol, and most preferably from 3 500 to 6 000 g/mol.

According to one embodiment of the present invention, the calcium carbonate-comprising material provided in process step a) is natural ground calcium carbonate and/or precipitated calcium carbonate, preferably an aqueous suspension of natural ground calcium carbonate and/or precipitated calcium carbonate having a solids content within the range of 1 wt. % to 90 wt. %, preferably 3 wt. % to 60 wt. %, more preferably 5 wt. % to 40 wt. %, and most preferably 10 wt. % to 25 wt. %, based on the weight of the aqueous suspension Process Step b)

According to step b) of the process of the present invention, at least one $H_3O^+$ ion donor is provided. An "$H_3O^+$ ion donor" in the context of the present invention is a Brønsted acid and/or an acid salt, i.e. a salt containing an acidic hydrogen.

The at least one $H_3O^+$ ion donor may be any strong acid, medium-strong acid, or weak acid, or a mixture thereof, generating $H_3O^+$ ions under the preparation conditions. According to the present invention, the at least one $H_3O^+$ ion donor can also be an acid salt, generating $H_3O^+$ ions under the preparation conditions.

According to one embodiment, the at least one $H_3O^+$ ion donor is a strong acid having a p$K_a$ of 0 or less at 20° C. According to another embodiment, the at least one $H_3O^+$ donor is a medium-strong acid having a p$K_a$ value from 0 to 2.5 at 20° C.

If the p$K_a$ at 20° C. is 0 or less, the acid is preferably selected from sulphuric acid, hydrochloric acid, or mixtures thereof. If the p$K_a$ at 20° C. is from 0 to 2.5, the $H_3O^+$ ion donor is preferably selected from $H_2SO_3$, $H_3PO_4$, oxalic acid, or mixtures thereof. The at least one $H_3O^+$ ion donor can also be an acid salt, for example, $HSO_4^-$ or $H_2PO_4^-$, being at least partially neutralized by a corresponding cation such as Li$^+$, Na$^+$ or K$^+$, or $HPO_4^{2-}$, being at least partially neutralised by a corresponding cation such as Li$^+$, Na$^+$, K$^+$, Mg$^{2+}$ or Ca$^{2+}$. The at least one $H_3O^+$ ion donor can also be a mixture of one or more acids and one or more acid salts.

According to still another embodiment, the at least one $H_3O^+$ ion donor is a weak acid having a p$K_a$ value of greater than 2.5 and less than or equal to 7, when measured at 20° C., associated with the ionisation of the first available hydrogen, and having a corresponding anion, which is capable of forming water-soluble calcium salts. Subsequently, at least one water-soluble salt, which in the case of a hydrogen-containing salt has a p$K_a$ of greater than 7, when measured at 20° C., associated with the ionisation of the first available hydrogen, and the salt anion of which is capable of forming water-insoluble calcium salts, is additionally provided. According to the preferred embodiment, the weak acid has a p$K_a$ value from greater than 2.5 to 5 at 20° C., and more preferably the weak acid is selected from the group consisting of acetic acid, formic acid, propanoic acid, and mixtures thereof. Exemplary cations of said water-soluble salt are selected from the group consisting of potassium, sodium, lithium and mixtures thereof. In a more preferred embodiment, said cation is sodium or potassium. Exemplary anions of said water-soluble salt are selected from the group consisting of phosphate, dihydrogen phosphate, monohydrogen phosphate, oxalate, silicate, mixtures thereof and hydrates thereof. In a more preferred embodiment, said anion is selected from the group consisting of phosphate, dihydrogen phosphate, monohydrogen phosphate, mixtures thereof and hydrates thereof. In a most preferred embodiment, said anion is selected from the group consisting of dihydrogen phosphate, monohydrogen phosphate, mixtures thereof and hydrates thereof. Water-soluble salt addition may be performed dropwise or in one step. In the case of drop wise addition, this addition preferably takes place within a time period of 10 minutes. It is more preferred to add said salt in one step.

According to one embodiment of the present invention, the at least one $H_3O^+$ ion donor is selected from the group consisting of hydrochloric acid, sulphuric acid, sulphurous acid, phosphoric acid, citric acid, oxalic acid, an acidic salt, acetic acid, formic acid, and mixtures thereof. Preferably the at least one $H_3O^+$ ion donor is selected from the group consisting of hydrochloric acid, sulphuric acid, sulphurous acid, phosphoric acid, oxalic acid, $H_2PO_4^-$, being at least partially neutralised by a cation selected from $Li^+$, $Na^+$ and/or $HPO_4^{2-}$, being at least partially neutralised by a cation selected from $Li^+$, $Na^+$, $Mg^{2+}$, and/or $Ca^{2+}$, and mixtures thereof, more preferably the at least one $H_3O^+$ ion donor is selected from the group consisting of hydrochloric acid, sulphuric acid, sulphurous acid, phosphoric acid, oxalic acid, or mixtures thereof, and most preferably, the at least one $H_3O^+$ ion donor is phosphoric acid.

The at least one $H_3O^+$ ion donor can be provided in solid form or in form of a solution. According to a preferred embodiment, the at least one $H_3O^+$ ion donor is provided in form of a solution.

According to one embodiment the at least one $H_3O^+$ ion donor is provided in form of an aqueous solution comprising the at least one $H_3O^+$ ion donor in an amount from 0.1 to 100 wt. %, based on the total weight of the aqueous solution, preferably in an amount from 1 to 80 wt. %, more preferably in an amount from 10 to 50 wt. %, and most preferably in an amount from 20 to 40 wt. %.

According to one embodiment, the molar ratio of the at least one $H_3O^+$ ion donor to the calcium carbonate-comprising material is from 0.01 to 4, preferably from 0.02 to 2, more preferably from 0.05 to 1, and most preferably from 0.1 to 0.58.

According to another embodiment, the at least one $H_3O^+$ ion donor is provided in an amount from 1 to 40 wt. %, based on the total weight of the calcium carbonate-comprising material, preferably from 5 to 30 wt. %, more preferably from 10 to 20 wt. %, and most preferably from 15 to 18 wt. %.

Process Step c)

According to step c) of the process of the present invention at least one water-soluble metal cation source is provided.

According to one embodiment the at least one water-soluble metal cation source is selected from the group consisting of a water-soluble metal salt, a water-soluble transition metal complex, a water-soluble metal hydroxide, a water-soluble metal oxide, and mixtures thereof.

The water-soluble metal cation source may be selected from the group consisting of a water-soluble transition metal salt, a water-soluble group(III) metal salt, and mixtures thereof. According to one embodiment the water-soluble metal cation source is selected from the group consisting of water-soluble salts of aluminium, chromium, manganese, iron, cobalt, nickel, copper, zinc, silver, gold, zirconium, palladium, platinum, and mixtures thereof.

Examples of a suitable water-soluble aluminium salts are aluminium chloride ($AlCl_3$) or aluminium sulphate ($Al_2(SO_4)_3$). The water-soluble aluminium salt may be an anhydrous salt or a hydrate salt.

Examples of a suitable water-soluble chromium salt are chromium bromide ($CrBr_3$), chromium chloride ($CrCl_2$), chromium fluoride ($CrF_2$), chromium nitrate ($Cr(NO_3)_3$), or chromium perchlorate ($Cr(ClO_4)_3$). The water-soluble chromium salt may be an anhydrous salt or a hydrate salt.

Examples of a suitable water-soluble manganese salt are manganese bromide ($MnBr_2$), manganese chloride ($MnCl_2$), manganese nitrate ($Mn(NO_3)_2$), manganese sulphate ($MnSO_4$), manganese carbonate ($MnCO_3$), manganese(II) acetate, manganese(II) benzoate, manganese(II) formate, manganese(II) tartrate, or manganese(IT) phosphate. The water-soluble manganese salt may be an anhydrous salt or a hydrate salt.

Examples of a suitable water-soluble iron salt are iron bromide ($FeBr_2$), iron chloride ($FeCl_2$, $FeCl_3$), iron iodide ($FeI_2$), iron nitrate ($Fe(NO_3)_3$), potassium hexacyanoferrate ($K_4Fe(CN)_6$), ammonium iron sulphate ($(NH_4)_2Fe(SO_4)_2$, or iron sulphate ($FeSO_4$). The water-soluble iron salt may be an anhydrous salt or a hydrate salt.

Examples of a suitable water-soluble cobalt salt are cobalt bromide ($CuBr_2$), cobalt chloride ($CoCl_2$), cobalt chlorate ($Co(ClO_3)_2$), cobalt iodide ($CoI_2$), cobalt nitrate ($Co(NO_3)_2$), or cobalt sulphate ($CoSO_4$). The water-soluble cobalt salt may be an anhydrous salt or a hydrate salt.

Examples of a suitable water-soluble copper salt are copper bromide ($CuBr_2$), copper chloride ($CuCl_2$), copper nitrate ($Cu(NO_3)_2$), copper acetate ($C_4H_6CuO_4$), copper sulphate ($CuSO_4$), or copper iodide ($CuI_2$). The water-soluble copper salt may be an anhydrous salt or a hydrate salt.

Examples of a suitable water-soluble zinc salt are zinc bromide ($ZnBr_2$), zinc chloride ($ZnCl_2$), zinc nitrate ($Zn(NO_3)_2$), zinc iodide ($ZnI_2$), zinc sulphate, zinc(II) acetate, or zinc(II) citrate. The water-soluble zinc salt may be an anhydrous salt or a hydrate salt.

Examples of suitable water-soluble silver salts are silver perchlorate ($AgClO_4$) and silver nitrate ($AgNO_3$). The water-soluble silver salt may be an anhydrous salt or a hydrate salt.

Examples of a suitable water-soluble gold salts are gold (III) bromide, gold(III) chloride, or potassium dicyanoaurate (I) ($K[Au(CN)_2]$). The water-soluble gold salt may be an anhydrous salt or a hydrate salt.

An example of a suitable water-soluble zirconium salt is zirconium(IV) sulphate. The water-soluble zirconium salt may be an anhydrous salt or a hydrate salt.

Examples of suitable water-soluble palladium salts are palladium(II) sulphate, palladium(II) nitrate, tetraammine palladium hydrogen carbonate, or diamine dichloro palladium(II). The water-soluble palladium salt may be an anhydrous salt or a hydrate salt.

Examples of a suitable water-soluble platinum salts are platinum(IV) bromide, platinum(IV) chloride, $Na_2PtCl_6$, or $H_2PtCl_6$. The water-soluble platinum salt may be an anhydrous salt or a hydrate salt.

As used herein, a "hydrate" is an inorganic salt containing water molecules combined in a definite ratio as an integral part of the crystal. Depending on the number of water molecules per formula unit of salt, the hydrate may be designated as monohydrate, dihydrate, trihydrate, tetrahydrate, pentahydrate, hexahydrate, heptahydrate, octahydrate, nonahydrate, decahydrate, hemihydrates, etc.

Examples of water-soluble transition metal complexes are $Na_2PdCl_4$, $Na_2PtCl_4$, $Pd(OAc)_2$, $Pd(H_2NCH_2CH_2NH_2)Cl_2$, $PdCl_2$.

Water-soluble metal hydroxides or water-soluble metal oxides may also be a suitable metal cation source.

According to a preferred embodiment the water-soluble metal cation source is a water-soluble salt of copper and/or zinc, and more preferably the water-soluble metal cation source is selected from the group consisting of copper nitrate, copper sulphate, copper acetate, copper chloride, copper bromide, copper iodide, zinc nitrate, zinc sulphate, zinc acetate, zinc chloride, zinc bromide, zinc iodide, hydrates thereof, and mixtures thereof.

According to one embodiment the at least one water-soluble metal cation source is provided in an amount from 0.01 to 60 wt. %, based on the total weight of the calcium carbonate-comprising material, preferably from 0.05 to 50 wt. %, more preferably from 0.1 to 25 wt. %, and most preferably from 0.5 to 10 wt. %. According to an exemplary embodiment, the at least one water-soluble metal cation source is provided in an amount from 1 to 10 wt. %, based on the total weight of the calcium carbonate-comprising material, preferably from 2 to 8 wt. %, more preferably from 3 to 6 wt. %, and most preferably from 4 to 5 wt. %.

The at least one water soluble metal salt, water soluble metal hydroxide, water soluble metal oxide or mixtures thereof can be provided in form of a solution, a suspension or as a dry material.

According to one embodiment the at least one water soluble metal salt, water soluble metal hydroxide, water soluble metal oxide or mixtures thereof is provided as dry material. The dry material may be in the form of powder, flakes, granules etc. and most preferably is in the form of a powder.

According to another embodiment the at least one water-soluble metal cation source is provided in form of an aqueous solution or aqueous suspension, preferably an aqueous solution, comprising the at least one water-soluble metal cation source in an amount from 0.01 to 10 wt-%, based on the total weight of the aqueous solution, preferably in an amount from 0.1 to 8 wt. %, more preferably in an amount from 0.4 to 5 wt. %, and most preferably in an amount from 0.8 to 2 wt. %.

Process Step d)

According to step d) of the process of the present invention, the calcium carbonate-comprising material of step a) is treated with the at least one $H_3O^+$ ion donor of step b) and carbon dioxide in an aqueous medium to form a suspension of surface-reacted calcium carbonate, wherein the carbon dioxide is formed in-situ by the $H_3O^+$ ion donor treatment and/or is supplied from an external source, and wherein the at least one water-soluble metal cation source of step c) is added during step d).

The calcium carbonate-comprising material can be treated with the at least one $H_3O^+$ ion donor by providing an aqueous suspension of the calcium carbonate-comprising material and adding the at least one $H_3O^+$ ion donor to said suspension. The at least one $H_3O^+$ ion donor can be added to the suspension as a concentrated solution or a more diluted solution. As an alternative, it is also possible to treat the calcium carbonate-comprising material with the at least one $H_3O^+$ ion donor by adding the calcium carbonate-comprising material to a solution of the at least one $H_3O^+$ ion donor.

The least one $H_3O^+$ ion donor of step b) and the at least one water-soluble metal cation source of step c) may be provided in form of separate solutions and/or in form of combined solutions.

According to one embodiment, in step d) the calcium carbonate-comprising material is treated with a solution comprising the at least one $H_3O^+$ ion donor of step b) and the at least one water-soluble metal cation source of step c).

According to another embodiment, in step d) the calcium carbonate-comprising material is treated with a first solution comprising a first part of the at least one $H_3O^+$ ion donor of step b), and subsequently, with a second solution comprising the remaining part of the at least one $H_3O^+$ ion donor of step b) and the at least one water-soluble metal cation source of step c). The first solution may comprise less than or equal to 50 wt. % of the at least one $H_3O^+$ ion donor, based on the total amount of the at least one $H_3O^+$ ion donor, preferably less than or equal to 40 wt. %, more preferably less than or equal to 30 wt. %, and most preferably less than or equal to 20 wt. %. For example, the first solution may comprise from 0.1 to 50 wt. % of the at least one $H_3O^+$ ion donor, based on the total amount of the at least one $H_3O^+$ ion donor, preferably from 1 to 40 wt. %, more preferably from 5 to 30 wt. %, and most preferably from 10 to 20 wt. %.

According to still another embodiment, in step b) a first $H_3O^+$ ion donor and a second $H_3O^+$ ion donor are provided, and in step d) the calcium carbonate-comprising material is treated with a first solution comprising the first $H_3O^+$ ion donor, and subsequently, with a second solution comprising the second $H_3O^+$ ion donor and the at least one water-soluble metal cation source of step c).

According to one embodiment in step d) the calcium carbonate-comprising material is treated with a first solution comprising a first part of the at least one $H_3O^+$ ion donor of step b), and subsequently, with a second solution comprising the remaining part of the at least one $H_3O^+$ ion donor of step b) and the at least one water-soluble metal cation source of step c), wherein the first solution comprises less than 50 wt. % of the at least one $H_3O^+$ ion donor, based on the total amount of the at least one $H_3O^+$ ion donor, preferably less than 40 wt. %, more preferably less than 30 wt. %, and most preferably less than 20 wt. %.

According to a preferred embodiment in step d) the calcium carbonate-comprising material is treated with a solution comprising the at least one $H_3O^+$ ion donor in an amount from 1 to 80 wt. %, preferably in an amount from 2 to 50 wt. %, more preferably in an amount from 5 to 30 wt. %, and most preferably in an amount from 10 to 20 wt. %, based on the total weight of the aqueous solution, and the at least one water-soluble metal cation source in an amount from 0.01 to 10 wt. %, preferably in an amount from 0.1 to 8 wt. %, more preferably in an amount from 0.4 to 5 wt. %, and most preferably in an amount from 0.8 to 2 wt. %, based on the total weight of the aqueous solution.

According to a preferred embodiment, the calcium carbonate-comprising material is a natural ground calcium carbonate, the at least one $H_3O^+$ ion donor is phosphoric acid, the at least one water-soluble metal cation source is selected from the group consisting of copper nitrate, copper sulphate, copper acetate, copper chloride, copper bromide, copper iodide, zinc nitrate, zinc sulphate, zinc acetate, zinc chloride, zinc bromide, zinc iodide, hydrates thereof, and mixtures thereof, and in step d) the calcium carbonate-comprising material is treated with a solution comprising the at least one $H_3O^+$ ion donor of step b) and the at least one water-soluble metal cation source of step c).

According to a preferred embodiment, the calcium carbonate-comprising material is a natural ground calcium carbonate, the at least one $H_3O^+$ ion donor is phosphoric acid, the at least one water-soluble metal cation source is selected from the group consisting of copper nitrate, copper sulphate, copper acetate, copper chloride, copper bromide, copper iodide, zinc nitrate, zinc sulphate, zinc acetate, zinc chloride, zinc bromide, zinc iodide, hydrates thereof, and mixtures thereof, and in step d) the calcium carbonate-comprising material is treated with a first solution comprising a first part of the at least one $H_3O^+$ ion donor of step b), and subsequently, with a second solution comprising the remaining part of the at least one $H_3O^+$ ion donor of step b) and the at least one water-soluble metal cation source of step c).

According to one embodiment, the at least one $H_3O^+$ ion donor is added over a time period of at least 1 min, preferably at least 5 min, and more preferably at least 10 min. In case the calcium carbonate-comprising material is treated with a first and a second solution, the first solution comprising a first part of the at least one $H_3O^+$ ion donor or a first $H_3O^+$ ion donor may be added over a time period of at least 1 min, preferably at least 5 min, and more preferably at least 10 min, and the second solution comprising the remaining part of the at least one $H_3O^+$ ion donor or the second $H_3O^+$ ion donor and the at least one water-soluble metal cation source may be added over a time period of at least 1 min, preferably at least 5 min, and more preferably at least 10 min.

According to step d) of the process of the present invention, the calcium carbonate-comprising material is treated with carbon dioxide. If a strong acid such as sulphuric acid or hydrochloric acid is used for the $H_3O^+$ ion donor treatment of the calcium carbonate-comprising material, the carbon dioxide is automatically formed. Alternatively or additionally, the carbon dioxide can be supplied from an external source.

$H_3O^+$ ion donor treatment and treatment with carbon dioxide can be carried out simultaneously which is the case when a strong or medium-strong acid is used. It is also possible to carry out $H_3O^+$ ion donor treatment first, e.g. with a medium strong acid having a $pK_a$ in the range of 0 to 2.5 at 20° C., wherein carbon dioxide is formed in situ, and thus, the carbon dioxide treatment will automatically be carried out simultaneously with the $H_3O^+$ ion donor treatment, followed by the additional treatment with carbon dioxide supplied from an external source.

Preferably, the concentration of gaseous carbon dioxide in the suspension formed in step d) is, in terms of volume, such that the ratio (volume of suspension):(volume of gaseous $CO_2$) is from 1:0.05 to 1:20, even more preferably 1:0.05 to 1:5.

In a preferred embodiment, the $H_3O^+$ ion donor treatment step and/or the carbon dioxide treatment of step d) are repeated at least once, more preferably several times.

Subsequent to the $H_3O^+$ ion donor treatment and carbon dioxide treatment, the pH of the aqueous suspension, measured at 20° C., naturally reaches a value of greater than 6.0, preferably greater than 6.5, more preferably greater than 7.0, even more preferably greater than 7.5, thereby preparing the surface-reacted natural or precipitated calcium carbonate as an aqueous suspension having a pH of greater than 6.0, preferably greater than 6.5, more preferably greater than 7.0, even more preferably greater than 7.5.

According to one embodiment of the present invention, step d) is carried out at a temperature from 20 to 90° C., preferably from 30 to 85° C., more preferably from 40 to 80° C., even more preferably from 50 to 75° C., and most preferably from 60 to 70° C.

According to one embodiment, the process step d) is carried out for at least 1 min, preferably for at least 5 min, more preferably for at least 10 min, and most preferably for at least 15 min.

Process Step d) may be carried out by simply adding, for example, by pouring, discharging, or injecting, the at least one $H_3O^+$ ion donor and/or the at least one water-soluble metal cation source into the calcium carbonate-comprising material. According to one embodiment, process step d) is carried out under mixing conditions. Suitable mixing methods are known to the skilled person. Examples of suitable mixing methods are shaking, mixing, stirring, agitating, ultrasonication, or inducing a turbulent or laminar flow by means such as baffles or lamellae. Suitable mixing equipment is known to the skilled person, and may be selected, for example, from stirrers, such as rotor stator systems, blade stirrers, propeller stirrers, turbine stirrers, or anchor stirrers, static mixers such as pipes including baffles or lamellae. According to an exemplary embodiment of the present invention, a rotor stator stirrer system is used.

According to another exemplary embodiment, in step d) the formed suspension is mixed so as to develop an essentially laminar flow. The skilled person will adapt the mixing conditions such as the mixing speed and temperature according to his process equipment.

Depending on the amount of water that is introduced during step d) by contacting the aforementioned compounds, additional water may be introduced during process step d), for example, in order to control and/or maintain and/or achieve the desired solids content or Brookfield viscosity of the obtained aqueous suspension. According to one embodiment the solids content of the mixture obtained in step d) is from 5 to 80 wt. %, preferably from 20 to 78 wt. %, based on the total weight of the mixture. The Brookfield viscosity of the obtained aqueous suspension may be from 10 to 10 000 mPa·s, preferably from 50 to 1 000 mPa·s.

The process of the present invention may be carried out in form of a continuous process or a batch process, preferably in from of a continuous process.

Additional Process Steps

According to one embodiment, the process of the present invention further comprises a step of agitating the aqueous suspension after step d). Preferably, the suspension is agitated for at least 1 min, preferably for at least 5 min, more preferably for at least 10 min, and most preferably for at least 15 min.

The aqueous suspension of surface-reacted calcium carbonate may be further processed, e.g., the surface-reacted calcium carbonate may be separated from the aqueous suspension and/or subjected to a drying step.

According to one embodiment, the process of the present invention further comprises a step c) of separating the surface-reacted calcium carbonate from the aqueous suspension obtained in step d). Thus, a process for manufacturing a surface-reacted calcium carbonate may comprise the following steps:

a) providing a calcium carbonate-comprising material,
b) providing at least one $H_3O^+$ ion donor, c) providing at least one water-soluble metal cation source, and d) treating the calcium carbonate-comprising material of step a) with the at least one $H_3O^+$ ion donor of step b) and carbon dioxide in an aqueous medium to form an aqueous suspension of surface-reacted calcium carbonate, wherein the carbon dioxide is formed in-situ by the $H_3O^+$ ion donor treatment and/or is supplied from an external source, and wherein the at least one water-soluble metal cation source of step c) is added during step d), and e) separating the surface-reacted calcium carbonate from the aqueous suspension obtained from step d).

The surface-reacted calcium carbonate obtained from step d) may be separated from the aqueous suspension by any conventional means of separation known to the skilled person. According to one embodiment of the present invention, in process step e) the surface-reacted calcium carbonate is separated mechanically and/or thermally. Examples of mechanical separation processes are filtration, e.g. by means of a drum filter or filter press, nanofiltration, or centrifugation. An example for a thermal separation process is a concentrating process by the application of heat, for example, in an evaporator. According to a preferred embodiment, in process step e) the surface-reacted calcium carbonate is separated mechanically, preferably by filtration and/or centrifugation.

After separation, the surface-reacted calcium carbonate can be dried in order to obtain a dried surface-reacted calcium carbonate. According to one embodiment, the process of the present invention further comprises a step f) of drying the surface-reacted calcium carbonate after step d) or after step e), if present, at a temperature in the range from 60 to 600° C., preferably until the moisture content of the surface-reacted calcium carbonate is between 0.01 and 5 wt. %, based on the total weight of the dried surface-reacted calcium carbonate.

According to one embodiment of the present invention, a process for manufacturing a dried surface-reacted calcium carbonate is provided comprising the following steps:

a) providing a calcium carbonate-comprising material, b) providing at least one $H_3O^+$ ion donor, c) providing at least one water-soluble metal cation source, and d) treating the calcium carbonate-comprising material of step a) with the at least one $H_3O^+$ ion donor of step b) and carbon dioxide in an aqueous medium to form an aqueous suspension of surface-reacted calcium carbonate, wherein the carbon dioxide is formed in-situ by the $H_3O^+$ ion donor treatment and/or is supplied from an external source, and wherein the at least one water-soluble metal cation source of step c) is added during step d), e) separating the surface-reacted calcium carbonate from the aqueous suspension obtained from step d), and f) drying the surface-reacted calcium carbonate.

In general, the drying step f) may take place using any suitable drying equipment and can, for example, include thermal drying and/or drying at reduced pressure using equipment such as an evaporator, a flash drier, an oven, a spray drier and/or drying in a vacuum chamber. The drying step f) can be carried out at reduced pressure, ambient pressure or under increased pressure. For temperatures below 100° C. it may be preferred to carry out the drying step under reduced pressure.

According to one preferred embodiment, the separation is carried out by a thermal method. This may allow to dry the surface-reacted calcium carbonate subsequently without changing the equipment.

According to one embodiment, in process step f) the surface-reacted calcium carbonate is dried until the moisture content of the formed surface-reacted calcium carbonate is less than or equal to 1.0 wt. %, based on the total weight of the dried surface-reacted calcium carbonate, preferably less than or equal to 0.5 wt. %, and more preferably less than or equal to 0.2 wt. %. According to another embodiment, in process step d) the surface-reacted calcium carbonate is dried until the moisture content of the formed surface-reacted calcium carbonate is between 0.01 and 0.15 wt. %, preferably between 0.02 and 0.10 wt. %, and more preferably between 0.03 and 0.07 wt. %, based on the total weight of the dried surface-reacted calcium carbonate.

The Surface-reacted Calcium Carbonate

According to a further aspect of the present invention, a surface-reacted calcium carbonate is provided, wherein the surface-reacted calcium carbonate is obtainable by a process of the present invention. Thus, the surface-reacted calcium carbonate may be obtained by a process comprising the steps of:

a) providing a calcium carbonate-comprising material, b) providing at least one $H_3O^+$ ion donor, c) providing at least one water-soluble metal cation source, and d) treating the calcium carbonate-comprising material of step a) with the at least one $H_3O^+$ ion donor of step b) and carbon dioxide in an aqueous medium to form an aqueous suspension of surface-reacted calcium carbonate, wherein the carbon dioxide is formed in-situ by the $H_3O^+$ ion donor treatment and/or is supplied from an external source, and wherein the at least one water-soluble metal cation source of step c) is added during step d).

The surface-reacted calcium carbonate may have different particle shapes, such as e.g. the shape of roses, golf balls and/or brains.

According to one embodiment the surface-reacted calcium carbonate has a specific surface area of from 15 $m^2/g$ to 200 $m^2/g$, preferably from 20 $m^2/g$ to 180 $m^2/g$, more preferably from 25 $m^2/g$ to 160 $m^2/g$, even more preferably from 27 $m^2/g$ to 150 $m^2/g$, most preferably from 30 $m^2/g$ to 140 $m^2/g$, measured using nitrogen and the BET method. For example, the surface-reacted calcium carbonate may have a specific surface area of from 27 $m^2/g$ to 100 $m^2/g$, measured using nitrogen and the BET method. The BET specific surface area in the meaning of the present invention is defined as the surface area of the particles divided by the mass of the particles. As used therein the specific surface area is measured by adsorption using the BET isotherm (ISO 9277:1995) and is specified in $m^2/g$.

According to one embodiment, the surface-reacted calcium carbonate has a volume determined median particle size $d_{50}(vol)$ from 1 to 75 µm, preferably from 2 to 50 µm, more preferably from 3 to 40 µm, even more preferably from 4 to 30 µm, and most preferably from 5 to 15 µm, and/or a volume determined top cut particle size $d_{98}(vol)$ from 2 to 150 µm, preferably from 4 to 100 µm, more preferably from 6 to 80 µm, even more preferably from 8 to 60 µm, and most preferably from 10 to 30 µm.

The surface-reacted calcium carbonate may have an intra-particle intruded specific pore volume in the range from 0.1 to 2.3 $cm^3/g$, preferably from 0.2 to 2.0 $cm^3/g$, more preferably from 0.4 to 1.8 cm$^3$/g and most preferably from 0.6 to 1.6 cm$^3$/g, calculated from mercury porosimetry measurement.

The intra-particle pore size of the surface-reacted calcium carbonate preferably is in a range of from 0.004 to 1.6 µm, more preferably in a range of between 0.005 to 1.3 µm, especially preferably from 0.006 to 1.15 µm and most preferably of 0.007 to 1.0 µm, e.g. 0.1 to 0.6 µm determined by mercury porosimetry measurement.

According to one embodiment, a surface-reacted calcium carbonate is provided, wherein the surface-reacted calcium carbonate comprises a calcium carbonate-comprising material, at least one water-insoluble calcium salt other than calcium carbonate, and at least one water-insoluble metal cation salt. According to one embodiment the surface-reacted calcium carbonate comprises (i) a specific surface area of from 15 to 200 m$^2$/g measured using nitrogen and the BET method according to ISO 9277:2010;

(ii) an intra-particle intruded specific pore volume in the range of from 0.1 to 2.3 cm$^3$/g calculated from mercury porosimetry measurement; and (iii) a ratio of the at least one water-insoluble calcium salt to calcium carbonate in the range of from 1:99 to 99:1 by weight, and (iv) a ratio of the at least one water-insoluble metal cation salt to calcium carbonate in the range of from 0.00001:1 to 0.1:1 by weight.

According to one embodiment the at least one water-insoluble calcium salt is selected from the group consisting of octacalcium phosphate, hydroxyapatite, chlorapatite, fluorapatite, carbonate apatite, preferably the at least one water-insoluble calcium salt is hydroxyapatite. According to a further embodiment, the ratio of the at least one water-insoluble calcium salt to calcium carbonate, preferably calcite, aragonite and/or vaterite, is in the range of from 1:9 to 9:1, preferably from 1:7 to 8:1, more preferably from 1:5 to 7:1, and even more preferably from 1:4 to 7:1 by weight. According to an exemplary embodiment, the surface-reacted calcium carbonate comprises a ratio of hydroxyapatite to calcite in the range of from 1:99 to 99:1 by weight, preferably in the range of from 1:9 to 9:1 by weight.

According to one embodiment, the ratio of the at least one water-insoluble metal cation salt to calcium carbonate, preferably calcite, aragonite and/or vaterite, is in the range of from 0.0001:1 to 0.1:1 by weight, and preferably from 0.001 to 0.01 by weight.

The surface-reacted calcium carbonate obtainable by a process of the present invention can be provided in form of a suspension of surface-reacted calcium carbonate, as a separated surface-reacted calcium carbonate or as a dried surface-reacted calcium carbonate. According to a preferred embodiment surface-reacted calcium carbonate is a dried surface-reacted calcium carbonate.

In case the surface-reacted calcium carbonate has been dried, the moisture content of the dried surface-reacted calcium carbonate can be between 0.01 and 5 wt. %, based on the total weight of the dried surface-reacted calcium carbonate. According to one embodiment, the moisture content of the dried surface-reacted calcium carbonate is less than or equal to 1.0 wt. %, based on the total weight of the dried surface-reacted calcium carbonate, preferably less than or equal to 0.5 wt. %, and more preferably less than or equal to 0.2 wt. %. According to another embodiment, the moisture content of the dried surface-reacted calcium carbonate is between 0.01 and 0.15 wt. %, preferably between 0.02 and 0.10 wt. %, and more preferably between 0.03 and 0.07 wt. %, based on the total weight of the dried surface-reacted calcium carbonate.

The inventive surface-reacted calcium carbonate may also be provided and/or used in form of a composition. According to one aspect of the present invention, a composition is provided comprising a surface-reacted calcium carbonate according to present invention. Said composition may further comprise an additional surface-reacted calcium carbonate, wherein the additional surface-reacted calcium carbonate is a reaction product of natural ground calcium carbonate or precipitated calcium carbonate with carbon dioxide and at least one H$_3$O$^+$ ion donor, wherein the carbon dioxide is formed in-situ by the H$_3$O$^+$ ion donor treatment and/or is supplied from an external source. Alternatively, or additionally other filler materials such as natural ground calcium carbonate, precipitated calcium carbonate, dolomite, and mixtures thereof may be present. The composition may comprise the surface-reacted calcium carbonate according to present invention in an amount of at least 20 wt. %, based on the total weight of the composition, preferably at least 40 wt. %, more preferably at least 60 wt. %, and most preferably at least 80 wt. %.

The following paragraphs are intended to refer to the aqueous suspension of surface-reacted calcium carbonate, the separated surface-reacted calcium carbonate as well as the dried surface-reacted calcium carbonate.

The inventors surprisingly found that by the inventive process a surface-reacted calcium carbonate is formed which provides additional functionalities due to the incorporation of metal cations into the structure of the surface-reacted calcium carbonate. It was found that said functionalities can be tailored for the desired application by selecting an appropriate water-soluble metal cation source.

For example, the inventors of the present invention found that the surface-reacted calcium carbonate may exhibit antimicrobial activity in dry products or wet products, preferably dry products. Therefore, the inventive surface-reacted calcium carbonate can be used in suspensions, dispersions or slurries of minerals, fillers or pigments, which are typically employed in the paper, paint, rubber and plastics industries as coatings, fillers, extenders and pigments for papermaking as well as aqueous lacquers and paints intended for the preparation of dry or wet products, wherein the dry products are preferred. The inventive surface-reacted calcium carbonate may also substitute conventional fillers completely or partially. Since both the surface-reacted calcium carbonate is resistant to water, a long lasting antimicrobial effect can be provided by the inventive surface-reacted calcium carbonate. Thus, the inventive surface-reacted calcium carbonate can even be used in articles, which involve contact with water or aqueous liquids or are subjected regularly to water washing, such as paints or cloths.

Moreover, it was found that the inventive surface-reacted calcium carbonate may release minor amounts of metal cations, i.e. in the ppm range, and thus, may be used as micronutrient delivery agent and plant protection product on the same time. For example, in case the metal cation is copper the surface-reacted calcium carbonate may be used to replace conventional plant protection products such as the Bordeaux mixture used in vineyard treatments.

According to one embodiment, the inventive surface-reacted calcium carbonate is used as metal cation releaser, preferably as micronutrient delivery agent and/or plant protection product.

The surface-reacted calcium carbonate may be used for various applications.

According to one embodiment, the surface-reacted calcium carbonate obtainable by a process according to the present invention or a composition comprising the same is used in polymer applications, paper coating applications, paper making, paints, coatings, sealants, printing inks, adhesives, food, feed, pharmaceuticals, concrete, cement, cosmetics, water treatment, engineered wood applications, plasterboard applications, packaging applications and/or agricultural applications. Engineered wood applications may comprise the use in engineered wood products such as wood composites materials, preferably medium density fibreboards or chipboards. Preferably the surface-reacted calcium carbonate may be used as a dried surface-reacted calcium carbonate.

According to another embodiment, the surface-reacted calcium carbonate obtainable by a process according to the present invention or a composition comprising the same is used as preservative, for the control of odour, and/or for enhancing and/or mediating antimicrobial activity of a substrate. Preferably the surface-reacted calcium carbonate may be used as a dried surface-reacted calcium carbonate.

A preservative is a compound which can protect a substrate, dry and/or wet, from spoilage and/or degradation and/or destruction, and/or defacement and/or visible disfigurement due to the action of microorganisms and/or prevent growth of microorganisms on a substrate and/or in a substrate and/or prevent contamination of a substrate by microorganisms and/or prevent settlement of microorganisms on an substrate. According to a preferred embodiment, the preservative acts as a dry-film-preservative. The substrate is preferably in a solid state, such as a paper surface, a wood surface, a wall, the surface of a packaging material or the surface of a polymer article, but can also be in a wet state such as in an aqueous suspension.

"Odour" according to the present invention generally is defined as one or more volatilized chemical compounds, generally at a very low concentration, that humans or other animals perceive by the sense of olfaction. Accordingly, an "odorant" is a chemical compound that has a smell or odour, i.e. is sufficiently volatile to be transported to the olfactory system in the upper part of the nose.

Preferred odours to be controlled according to the present invention are odours which cause an unpleasant sensation, i.e. malodours, but are not limited thereto. Such odours may originate from odorants, which are preferably selected from the group comprising odorants contained in human and animal body liquids and secretion such as menses, blood, plasma, sanies; vaginal secretions, mucus, milk, urine; faeces; vomit and perspiration; odorants originating from putrefaction such as of human or animal tissue; food such as dairy products, meat and fish and fruit such as durian fruit.

According to one preferred embodiment of the present invention the odorants are selected from the group consisting of amines such as triethylamine, diethylamine, trimethylamine, diaminobutane, tetramethylenediamine, pentamethylenediamine, pyridine, indole, 3-methylindole; carboxylic acids such as propionic acid, butanoic acid, 3-methylbutanoic acid, 2-methylpropanoic acid, hexanoic acid; sulphur organic compounds such as thiols, e.g. methanethiol, phosphor organic compounds such as methylphosphine, dimethylphosphine, their derivatives and mixtures thereof; preferably the odorants are amines and most preferably the odorant is diethylamine. According to an exemplified embodiment of the present invention the odourants are diethylamine or a thiol, for example 2-propanethiol.

The surface-reacted calcium carbonate can also be used for enhancing and/or mediating the antimicrobial activity of a substrate, e.g. a sheet of paper, a cardboard, a polymer material, a paint, a wood surface, concrete, or a plant. According to a preferred embodiment, the antimicrobial activity is against at least one strain of bacteria and/or at least one strain of mould and/or at least one strain of yeast and/or at least one algae. Antimicrobial activity of a compound refers to a reduction of growth of microorganism and/or a reduction of viable microorganisms apparent in the presence of said compound. The expression "enhancing the antimicrobial activity" means that the antimicrobial activity of the substrate containing the inventive surface-reacted calcium carbonate is higher than the antimicrobial activity compared to a substrate not containing said filler. The expression "for mediating the antimicrobial activity of a substrate" means that no antimicrobial activity is apparent in a substrate without the inventive surface-reacted calcium carbonate.

According to one embodiment, the substrate is a paper, a cardboard, a polymer material, a paint, a wood surface, concrete, or a plant. According to one embodiment, the polymer material is a polymer film. A "film" in the meaning of the present invention is a sheet or layer of material having a median thickness which is small compared to its length and width. For example, the term "film" may refer to a sheet or layer of material having a median thickness of less than 200 µm, but more than 1 µm.

According to one embodiment the at least one strain of bacteria is selected from the group consisting of *Escherichia* sp., *Staphylococcus* sp., *Thermus* sp., *Propionibacterium* sp., *Rhodococcus* sp., *Panninobacter* sp., *Caulobacter* sp., *Brevundimonas* sp., *Asticcacaulis* sp., *Sphingomonas* sp., *Rhizobium* sp., *Ensifer* sp., *Bradyrhizobium* sp., *Tepidimonas* sp., *Tepidicella* sp., *Aquabacterium* sp., *Pelomonas* sp., *Alcaligenis* sp., *Achromobacter* sp., *Ralstonia* sp., *Limnobacter* sp., *Massilia* sp., *Hydrogenophaga* sp., *Acidovorax* sp., *Curvibacter* sp., *Delftia* sp., *Rhodoferax* sp., *Alishewanella* sp., *Stenotrophomonas* sp., *Dokdonella* sp., *Methylosinus* sp., *Hyphomicrobium* sp., *Methylosulfomonas* sp., *Methylobacteria* sp., *Pseudomonas* sp. such as *Pseudomonas mendocina*, *Enterococcus* sp., *Myroides* sp., *Burkholderia* sp., *Alcaligenes* sp. *Staphylococcus* sp. such as *Staphylococcus aureus*, *Escherichia* sp. such as *Escherichia* coli, and mixtures thereof.

According to one embodiment the at least one strain of mould is selected from the group comprising of *Acremonium* sp., *Alternaria* sp., *Aspergillus* sp. such as *Aspergillus niger*, *Aureobasidium* sp., such as *Aureobasidium pullulans*, *Cladosporium* sp., *Fusarium* sp., *Mucor* sp., *Penicillium* sp., such as *Penicillium funiculosum*, *Rhizopus* sp., *Stachybotrys* sp., *Trichoderma* sp., *Dematiaceae* sp., *Phoma* sp., *Eurotium* sp., *Scopulariopsis* sp., *Aureobasidium* sp., *Monilia* sp., *Botrytis* sp., *Stemphylium* sp., *Chaetomium* sp., *Mycelia* sp., *Neurospora* sp., *Ulocladium* sp., *Paecilomyces* sp., *Wallemia* sp., *Curvularia* sp., and mixtures thereof.

According to one embodiment the at least one strain of yeast is selected from the group comprising Saccharomycotina, Taphrinomycotina, Schizosaccharomycetes, Basidiomycota, Agaricomycotina, Tremellomycetes, Pucciniomycotina, Microbotryomycetes, *Candida* sp. such as *Candida albicans, Candida tropicalis, Candida stellatoidea, Candida glabrata, Candida krusci, Candida guilliermondii, Candida viswanathii, Candida lusitaniae* and mixtures thereof, *Yarrowia* sp. such as *Yarrowia lipolytica*, *Cryptococcus* sp. such as *Cryptococcus gattii* and *Cryptococcus neofarmans*, *Zygosaccharomyces* sp., *Rhodotorula* sp. such as *Rhodotorula mucilaginosa*, and mixtures thereof.

According to a preferred embodiment of the present invention, the at least one strain of bacteria is selected from the group consisting of *Escherichia coli, Staphylococcus aureus, Pseudomonas putida, Pseudomonas mendocina, Pseudomonas oleovorans, Pseudomonas fluorescens, Pseudomonas alcaligenes, Pseudomonas pseudoalcaligenes, Pseudomonas entomophila, Pseudomonas syringae, Methylobacterium extorquens, Methylobacterium radiotolerants, Methylobacterium dichloromethanicum, Methylobacterium organophilu, Hyphomicrobium zavarzini, Enterococcus faccalis, Myroides odoratus, Pseudomonas acruginosa, Pseudomonas orizyhabitans, Burkholderia cepacia, Alcaligenes faecalis* and *Sphingomonas paucimobilis* and mixtures thereof and/or the at least one strain of mould is selected from the group comprising of *Penicillium funiculosum, Aspergillus niger, Aureobasidium pullulans, Alternaria alternate, Cladosporium cladosporioides, Phoma violaceae, Ulocladium atrum, Aspergillus versicolor, Stachybotris chartarum, Penicillium purpurogenum, Rhodotorula mucilaginosa* and/or the at least one strain of yeast is selected from the group of *Candida albicans* and/or the at least one strain of alga is selected from the group of *Nostoc commune, Gloeocapsa alpicola* (syn. *Anacystis montana*), *Klebsormidium flaccidum, Stichococcus bacillaris, Pseudokirchneriella subcapitata, Desmodesmus subspicatus, Navicula pelliculosa, Anabaena flosaquae, Synechococcus leopoliensis*, and mixtures thereof.

According to still another embodiment, the surface-reacted calcium carbonate obtained by the process of the present invention is used for enhancing the electrical conductivity of a substrate.

The inventive surface-reacted calcium carbonate may be incorporated into an article in order to provide an article with enhanced antimicrobial activity and/or enhanced electrical conductivity. According to a further aspect of the present invention, an article is provided comprising a surface-reacted calcium carbonate obtainable by a process according to the present invention or a composition comprising the same, wherein the article is selected from paper products, engineered wood products, plasterboard products, polymer products, hygiene products, medical products, healthcare products, filter products, woven materials, nonwoven materials, geotextile products, agriculture products, horticulture products, clothing, footwear products, baggage products, household products, industrial products, packaging products, building products, and construction products.

The scope and interest of the invention will be better understood based on the following examples which are intended to illustrate certain embodiments of the present invention and are non-limitative.

EXAMPLES

1. Measurement Methods

In the following, measurement methods implemented in the examples are described.

Particle Size Distribution

Volume determined median particle size $d_{50}(vol)$ and the volume determined top cut particle size $d_{98}(vol)$ was evaluated using a Malvern Mastersizer 2000 Laser Diffraction System (Malvern Instruments Plc., Great Britain). The $d_{50}$ or $d_{98}$ value, measured using a Malvern Mastersizer 2000 Laser Diffraction System, indicates a diameter value such that 50% or 98% by volume, respectively, of the particles have a diameter of less than this value. The raw data obtained by the measurement were analysed using the Mie theory, with a particle refractive index of 1.57 and an absorption index of 0.005.

The weight determined median particle size $d_{50}(wt)$ was measured by the sedimentation method, which is an analysis of sedimentation behaviour in a gravimetric field. The measurement was made with a Sedigraph™ 5100 or 5120 of Micromeritics Instrument Corporation, USA. The method and the instrument are known to the skilled person and are commonly used to determine particle size distributions of fillers and pigments. The measurement was carried out in an aqueous solution of 0.1 wt. % $Na_4P_2O_7$. The samples were dispersed using a high speed stirrer and supersonicated.

Specific Surface Area (SSA)

The specific surface area was measured via the BET method according to ISO 9277:2010 using nitrogen, following conditioning of the sample by heating at 100° C. under vacuum for a period of 30 minutes. Prior to such measurements, the sample was filtered within a Buchner funnel, rinsed with deionised water and dried overnight at 90 to 100° C. in an oven. Subsequently, the dry cake was ground thoroughly in a mortar and the resulting powder was placed in a moisture balance at 130° C. until a constant weight was reached.

Intra-particle Intruded Specific Pore Volume (in $cm^3/g$)

The specific pore volume was measured using a mercury intrusion porosimetry measurement using a Micromeritics Autopore V 9620 mercury porosimeter having a maximum applied pressure of mercury 414 MPa (60 000 psi), equivalent to a Laplace throat diameter of 0.004 μm (~nm). The equilibration time used at each pressure step was 20 seconds. The sample material was sealed in a 3 $cm^3$ chamber powder penetrometer for analysis. The data were corrected for mercury compression, penetrometer expansion and sample material compression using the software Pore-Comp (Gane, P. A. C., Kettle, J. P., Matthews, G. P. and Ridgway, C. J., "Void Space Structure of Compressible Polymer Spheres and Consolidated Calcium Carbonate Paper-Coating Formulations", Industrial and Engineering Chemistry Research, 35(5), 1996, p 1753-1764.).

The total pore volume seen in the cumulative intrusion data can be separated into two regions with the intrusion data from 214 μm down to about 1-4 μm showing the coarse packing of the sample between any agglomerate structures contributing strongly. Below these diameters lies the fine inter-particle packing of the particles themselves. If they also have intra-particle pores, then this region appears bi-modal, and by taking the specific pore volume intruded by mercury into pores finer than the modal turning point, i.e. finer than the bi-modal point of inflection, the specific intra-particle pore volume is defined. The sum of these three regions gives the total overall pore volume of the powder, but depends strongly on the original sample compaction/settling of the powder at the coarse pore end of the distribution.

By taking the first derivative of the cumulative intrusion curve the pore size distributions based on equivalent Laplace diameter, inevitably including pore-shielding, are revealed. The differential curves clearly show the coarse agglomerate pore structure region, the inter-particle pore region and the intra-particle pore region, if present. Knowing the intra-particle pore diameter range it is possible to subtract the remainder inter-particle and inter-agglomerate pore volume from the total pore volume to deliver the desired pore volume of the internal pores alone in terms of the pore volume per unit mass (specific pore volume). The same principle of subtraction, of course, applies for isolating any of the other pore size regions of interest.

Inductively Coupled Plasma Optical Emission Spectrometry (ICP-OES)

Powder/filter cake were dissolved in $HNO_3$ (69%, trace select) and boiled for 3 minutes. After cooling, the solubilized samples were diluted with water. The solution was then filtered (0.2 and further diluted prior to analysis.

Aqueous samples were acidified with $HNO_3$ (69%, trace select), filtered (0.2 μm) and diluted if needed prior to analysis.

Analysis was made by ICP-OES on an Optima 3200 XL device (Copper lines Cu 224.7, Cu 324.752, Cu 327.393).

Antimicrobial Surface Activity Test

Fresh bacteria cultures of the bacteria *Staphylococcus aureus* DSM 346 strains were prepared by dilution streaking onto a tryptic soy agar plate (TSA, no. 236950, Becton Dickinson and Company, USA) and incubation for 16 to 20 h at 35° C.

To test the antimicrobial surface activity, the Japanese Standard Protocol JIS Z 2801 2000 was followed using fresh bacteria prepared as described above. The plating, counting and evaluation were done according to the Japanese Standard Protocol JIS Z 2801 2000 with the following amendments. For all coated samples, the bacteria were released after incubation from the test item in a petri dish using a sterile Drigalski spatula to massage the test item with medium, instead of using a stomacher bag and massaging the item by hand. Further for coated samples the test items were not sterilized with 70% ethanol prior analysis.

As described in the Japanese Standard Protocol JIS Z 2801 2000, the bacterial counts are reported as colony forming units per test item (cfu/test item) with 10 cfu/test item as limit of detection (LOD). Thereof the antimicrobial activity (R) of the test items was calculated as described in the Japanese Standard Protocol JIS Z 2801 2000. For it, after 24 h incubation at 35° C., the average number of viable bacteria on the test item (B) and the untreated control (A) are used to calculate the antimicrobial activity (R) using the following formula: $R=\log_{10}(A/B)$. If zero cfu were detected, a value of 10 cfu/test item was used for calculation of the limit of detection of the antimicrobial activity.

2. Mineral Materials

Surface-reacted Calcium Carbonate SRCC 1 (Inventive)

SRCC 1 was obtained by preparing 10 litres of an aqueous suspension of ground calcium carbonate in a mixing vessel by adjusting the solids content of a ground marble calcium carbonate from Hustadmarmor Norway having a mass based particle size distribution of 90% less than 2 μm, as determined by sedimentation, such that a solids content of 10 wt. %, based on the total weight of the aqueous suspension, is obtained.

In addition a solution was prepared containing 30% by mass phosphoric acid and 1% by mass of copper sulphate pentahydrate, $CuSO_4 \cdot 5H_2O$.

Whilst mixing the slurry, 1.1 kg of the phosphoric acid/copper sulphate solution was added to said suspension over a period of 10 minutes at a temperature of 70° C. Finally, after the addition of the phosphoric acid, the slurry was stirred for additional 5 minutes, before removing it from the vessel. Then, the slurry was dewatered by use of a filter press (with a maximum pressure of 4 bar) and dried in an oven at a temperature of 120° C. until dry. The obtained surface-reacted calcium carbonate had the following properties: $d_{50}=5.5$ μm, $d_{98}=8.6$ μm, $SSA=55.5$ $m^2g^{-1}$. The intra-particle intruded specific pore volume is 1.150 $cm^3/g$ (for the pore diameter range of 0.004 to 0.43 μm).

Surface-reacted Calcium Carbonate SRCC 2 (Inventive)

SRCC 2 was obtained by preparing 10 litres of an aqueous suspension of ground calcium carbonate in a mixing vessel by adjusting the solids content of a ground marble calcium carbonate from Hustadmarmor Norway having a mass based particle size distribution of 90% less than 2 μm, as determined by sedimentation, such that a solids content of 10 wt. %, based on the total weight of the aqueous suspension, is obtained.

In addition, two solutions were prepared. Solution A was prepared such that it contained 30 wt. %, based on the total weight of the aqueous solution, of phosphoric acid. Solution B was prepared by blending copper sulphate pentahydrate, $CuSO_4 \cdot 5H_2O$ into a solution of phosphoric acid such that the final solution contained 28.8 wt. %, based on the total weight of the aqueous solution, of phosphoric acid and 1.0 wt. %, based on the total weight of the aqueous solution, of copper ion.

Whilst mixing the slurry, 534 g of solution A was added to the 10 wt. % calcium carbonate suspension over a period of 5 minutes. Directly after solution A finished adding, 555 g of solution B was added to the suspension over a period of 6 minutes. Throughout the whole experiment the temperature of the suspension was maintained at 70° C. Finally, after the addition of solution B, the suspension was stirred for additional 5 minutes before removing it from the vessel and drying. The obtained surface-reacted calcium carbonate had the following properties: $d_{50}=5.4$ μm, $d_{98}=8.0$ μm, and $SSA=46.4$ $m^2g^{-1}$. The intra-particle intruded specific pore volume was 0.98 $cm^3/g$ (for the pore diameter range of 0.004 to 0.38 μm).

Surface-reacted Calcium Carbonate SRCC 3 (Inventive)

SRCC 3 was obtained by preparing 10 litres of an aqueous suspension of ground calcium carbonate in a mixing vessel by adjusting the solids content of a ground marble calcium carbonate from Hustadmarmor Norway having a mass based particle size distribution of 90% less than 2 μm, as determined by sedimentation, such that a solids content of 10 wt. %, based on the total weight of the aqueous suspension, is obtained.

In addition, two solutions were prepared. Solution A was prepared such that it contained 30 wt. %, based on the total weight of the aqueous solution, of phosphoric acid. Solution B was prepared by blending copper sulphate pentahydrate, $CuSO_4 \cdot 5H_2O$ into a solution of phosphoric acid such that the final solution contained 27.3 wt. %, based on the total weight of the aqueous solution, of phosphoric acid and 2.3 wt. %, based on the total weight of the aqueous solution, of copper ion.

Whilst mixing the slurry, 534 g of solution A was added to the 10 wt. % calcium carbonate suspension over a period of 5 minutes. Directly after solution A finished adding, 587 g of solution B was added to the suspension over a period of 6 minutes. Throughout the whole experiment the temperature of the suspension was maintained at 70° C. Finally, after the addition of solution B, the suspension was stirred for additional 5 minutes before removing it from the vessel and drying. The obtained surface-reacted calcium carbonate had the following properties: $d_{50}=5.2$ μm, $d_{98}=8.1$ μm, $SSA=30.3$ $m^2g^{-1}$. The intra-particle intruded specific pore volume was 1.00 $cm^3/g$ (for the pore diameter range of 0.004 to 0.30 μm).

Surface-reacted Calcium Carbonate SRCC 4 (Inventive)

SRCC 4 was obtained by preparing 10 litres of an aqueous suspension of ground calcium carbonate in a mixing vessel by adjusting the solids content of a ground marble calcium carbonate from Hustadmarmor Norway having a mass based particle size distribution of 90% less than 2 μm, as determined by sedimentation, such that a solids content of 10 wt. %, based on the total weight of the aqueous suspension, is obtained.

In addition, two solutions were prepared. Solution A was prepared such that it contained 30 wt. %, based on the total weight of the aqueous solution, of phosphoric acid. Solution B was prepared by blending copper sulphate pentahydrate, $CuSO_4 \cdot 5H_2O$ into a solution of phosphoric acid such that the final solution contained 25 wt. %, based on the total weight of the aqueous solution, of phosphoric acid and 4.2 wt. %, based on the total weight of the aqueous solution, of copper ion.

Whilst mixing the slurry, 534 g of solution A was added to the 10 wt. % calcium carbonate suspension over a period of 6 minutes. Directly after solution A finished adding, 640 g of solution B was added to the suspension over a period of 8 minutes. Throughout the whole experiment the temperature of the suspension was maintained at 70° C. Finally, after the addition of solution B, the suspension was stirred for additional 5 minutes before removing it from the vessel and drying. The obtained surface-reacted calcium carbonate had the following properties: $d_{50}$=5.0 µm, $d_{98}$=8.8 µm, SSA=34.2 $m^2g^{-1}$. The intra-particle intruded specific pore volume was 0.48 $cm^3/g$ (for the pore diameter range of 0.004 to 0.20 µm).

Surface-reacted Calcium Carbonate SRCC 5 (Inventive)

SRCC 5 was obtained by preparing 10 litres of an aqueous suspension of ground calcium carbonate in a mixing vessel by adjusting the solids content of a ground marble calcium carbonate from Hustadmarmor Norway having a mass based particle size distribution of 90% less than 2 µm, as determined by sedimentation, such that a solids content of 10 wt. %, based on the total weight of the aqueous suspension, is obtained.

In addition, two solutions were prepared. Solution A was prepared such that it contained 30 wt. %, based on the total weight of the aqueous solution, of phosphoric acid. Solution B was prepared by blending copper sulphate pentahydrate, $CuSO_4 \cdot 5H_2O$ into a solution of phosphoric acid such that the final solution contained 25 wt. %, based on the total weight of the aqueous solution, of phosphoric acid and 4.2 wt. %, based on the total weight of the aqueous solution, of copper ion.

Whilst mixing the slurry, 534 g of solution A was added to the 10 wt. % calcium carbonate suspension over a period of 5 minutes. Directly after solution A finished adding, 640 g of solution B was added to the suspension over a period of 15 minutes. Throughout the whole experiment the temperature of the suspension was maintained at 70° C. Finally, after the addition of solution B, the suspension was stirred for additional 5 minutes before removing it from the vessel and drying. The obtained surface-reacted calcium carbonate had the following properties: $d_{50}$=5.2 µm, $d_{98}$=8.9 µm, SSA=34.8 $m^2g^{-1}$. The intra-particle intruded specific pore volume was 0.49 $cm^3/g$ (for the pore diameter range of 0.004 to 0.22 µm).

Surface-reacted Calcium Carbonate SRCC 6 (Inventive)

SRCC 6 was obtained by preparing 10 litres of an aqueous suspension of ground calcium carbonate in a mixing vessel by adjusting the solids content of a ground marble calcium carbonate from Hustadmarmor Norway having a mass based particle size distribution of 90% less than 2 µm, as determined by sedimentation, such that a solids content of 10 wt. %, based on the total weight of the aqueous suspension, is obtained.

In addition, two solutions were prepared. Solution A was prepared such that it contained 30 wt. %, based on the total weight of the aqueous solution, of phosphoric acid. Solution B was prepared by blending zinc chloride anhydrous, $ZnCl_2$, into a solution of phosphoric acid such that the final solution contained 27.3 wt. %, based on the total weight of the aqueous solution, of phosphoric acid and 4.4 wt. %, based on the total weight of the aqueous solution, of zinc ion.

Whilst mixing the slurry, 534 g of solution A was added to the 10 wt. % calcium carbonate suspension over a period of 5 minutes. Directly after solution A finished adding, 587 g of solution B was added to the suspension over a period of 6 minutes. Throughout the whole experiment the temperature of the suspension was maintained at 70° C. Finally, after the addition of solution B, the suspension was stirred for additional 5 minutes before removing it from the vessel and drying. The obtained surface-reacted calcium carbonate had the following properties: $d_{50}$=5.5 µam, $d_{98}$=10.0 µm, SSA=43.2 $m^2g^{-1}$) The intra-particle intruded specific pore volume is 0.756 $cm^3/g$ (for the pore diameter range of 0.004 to 0.31 µm).

Surface-reacted Calcium Carbonate SRCC 7 (Inventive)

SRCC 7 was obtained by preparing 10 litres of an aqueous suspension of ground calcium carbonate in a mixing vessel by adjusting the solids content of a ground marble calcium carbonate from Hustadmarmor Norway having a mass based particle size distribution of 90% less than 2 µm, as determined by sedimentation, such that a solids content of 10 wt. %, based on the total weight of the aqueous suspension, is obtained.

In addition, two solutions were prepared. Solution A was prepared such that it contained 30 wt. %, based on the total weight of the aqueous solution, of phosphoric acid. Solution B was prepared by blending zinc chloride anhydrous, $ZnCl_2$, into a solution of phosphoric acid such that the final solution contained 25 wt. %, based on the total weight of the aqueous solution, of phosphoric acid and 8.0 wt. %, based on the total weight of the aqueous solution, of zinc ion.

Whilst mixing the slurry, 534 g of solution A was added to the 10 wt. % calcium carbonate suspension over a period of 5 minutes. Directly after solution A finished adding, 640 g of solution B was added to the suspension over a period of 7 minutes.

Throughout the whole experiment the temperature of the suspension was maintained at 70° C. Finally, after the addition of solution B, the suspension was stirred for additional 5 minutes before removing it from the vessel and drying. The obtained surface-reacted calcium carbonate had the following properties: $d_{50}$=8.3 µm, $d_{98}$=19.3 µm, SSA=30.1 $m^2g^{-1}$) The intra-particle intruded specific pore volume is 0.740 $cm^3/g$ (for the pore diameter range of 0.004 to 0.43 µm).

Surface-reacted Calcium Carbonate SRCC 8 (Inventive)

SRCC 8 was obtained by preparing 10 litres of an aqueous suspension of ground calcium carbonate in a mixing vessel by adjusting the solids content of a ground limestone calcium carbonate from Orgon, France having a mass based median particle size of 3 µm, as determined by sedimentation, such that a solids content of 10 wt. %, based on the total weight of the aqueous suspension, is obtained.

In addition, two solutions were prepared. Solution A was prepared such that it contained 30 wt. %, based on the total weight of the aqueous solution, of phosphoric acid. Solution B was prepared by blending zinc chloride anhydrous, $ZnCl_2$, into a solution of phosphoric acid such that the final solution contained 27.3 wt. %, based on the total weight of the aqueous solution, of phosphoric acid and 4.4 wt. %, based on the total weight of the aqueous solution, of zinc ion.

Whilst mixing the slurry, 534 g of solution A was added to the 10 wt. % calcium carbonate suspension over a period of 5 minutes. Directly after solution A finished adding, 587 g of solution B was added to the suspension over a period of 6 minutes. Throughout the whole experiment the temperature of the suspension was maintained at 70° C. Finally, after the addition of solution B, the suspension was stirred for additional 5 minutes before removing it from the vessel and drying. The obtained surface-reacted calcium carbonate had the following properties: $d_{50}$=11.0 µm, $d_{98}$=25.3 µm, SSA=27.6 $m^2g^{-1}$. The intra-particle intruded specific pore volume is 0.717 $cm^3/g$ (for the pore diameter range of 0.004 to 0.75 µm).

Powder 9 (Inventive)—a mix of SRCC 3 and SRCC 11

400 g of a 22 wt. % solid content filter cake from sample SRCC 3 were dispersed in 1 litres deionized water, agitated with a mechanical stirrer for approx. 20 minutes (300-350 rpm) and then filtered on a Buchner funnel. This procedure was repeated a second time, and, after the second washing step, the filter cake was dried in an oven (110° C.) and deagglomerated.

20 g of the above powder were then mixed with 180 g of SRCC 11.

Powder 10 (Inventive)—a mix of SRCC 5 and SRCC 11

400 g of a 24.5 wt. % solid content filter cake from sample SRCC 5 were dispersed in 1 L deionized water, agitated with a mechanical stirrer for Ca. 20 minutes (300-350 rpm) and then filtered on a Büchner funnel. This procedure was repeated a second time, and, after the second washing step, the filter cake was dried in an oven (110° C.) and deagglomerated.

20 g of the above powder were then mixed with 180 g of SRCC 11.

Surface-reacted calcium carbonate SRCC 11 (comparative)

SRCC 11 is a surface-reacted calcium carbonate ($d_{50}$=2.6 μm, BET=34.7 m$^2$/g, and an intra-particle intruded specific pore volume of 0.305 cm$^3$/g (for the pore diameter range of 0.004 to 0.19 μm), without further treatment.

Surface-reacted Calcium Carbonate SRCC 12 (Inventive)

SRCC 12 was obtained by preparing 0.5 a litre of an aqueous suspension of ground calcium carbonate in a mixing vessel by adjusting the solids content of a ground marble calcium carbonate from Hustadmarmor Norway having a mass based particle size distribution of 90% less than 2 μm, as determined by sedimentation, such that a solids content of 10 wt. %, based on the total weight of the aqueous suspension, is obtained.

In addition, a solution was prepared containing 29.1% by mass phosphoric acid and 3.1% by mass of chloroplatinic acid hexahydrate, $H_2PtCl_6 \cdot 6H_2O$.

Whilst mixing the slurry, 91.8 g of the phosphoric acid/chloroplatinic acid hexahydrate solution was added to said suspension over a period of 10 minutes at a temperature of 70° C. Finally, after the addition of the phosphoric acid, the slurry was stirred for additional 5 minutes, before removing it from the vessel. Then, the slurry was dried by use of a rotary evaporator. The obtained surface-reacted calcium carbonate had the following properties: $d_{50}$=8.8 μm, $d_{98}$=19.9 μm, SSA=53.9 m$^2$g$^{-1}$. The intra-particle intruded specific pore volume is 1.415 cm$^3$/g (for the pore diameter range of 0.004 to 0.67 μm).

Surface-Reacted Calcium Carbonate SRCC 13 (Inventive)

SRCC 13 was obtained by preparing 0.5 a litre of an aqueous suspension of ground calcium carbonate in a mixing vessel by adjusting the solids content of a ground marble calcium carbonate from Hustadmarmor Norway having a mass based particle size distribution of 90% less than 2 μm, as determined by sedimentation, such that a solids content of 10 wt. %, based on the total weight of the aqueous suspension, is obtained.

In addition, two solutions were prepared. Solution A was prepared such that it contained 30 wt. %, based on the total weight of the aqueous solution, of phosphoric acid. Solution B was prepared by blending chloroplatinic acid hexahydrate, $H_2PtCl_6 \cdot 6H_2O$ into a solution of phosphoric acid such that the final solution contained 28.2 wt. %, based on the total weight of the aqueous solution, of phosphoric acid and 2.3 wt. %, based on the total weight of the aqueous solution, of platinum ion.

Whilst mixing the slurry, 44.5 g of solution A was added to the 10 wt. % calcium carbonate suspension over a period of 5 minutes. Directly after solution A finished adding, 47.3 g of solution B was added to the suspension over a period of 5 minutes. Throughout the whole experiment the temperature of the suspension was maintained at 70° C. Finally, after the addition of solution B, the suspension was stirred for additional 5 minutes before removing it from the vessel and drying. The obtained surface-reacted calcium carbonate had the following properties: $d_{50}$=8.5 μm, $d_{98}$=18.1 μm, and SSA=57.8 m$^2$g$^{-1}$. The intra-particle intruded specific pore volume was 1.417 cm$^3$/g (for the pore diameter range of 0.004 to 0.67 μm).

3. Analysis

TABLE 1

Quantitative Rietveld analyses (XRD).

| Mineral | Formula | SRCC 11 (comparative) | SRCC 3 (inventive) | SRCC 4 (inventive) | SRCC 5 (inventive) |
|---|---|---|---|---|---|
| Calcite | $CaCO_3$ | 73.7 | 51.2 | 58.5 | 58.8 |
| Hydroxylapatite | $Ca_5(OH)(PO_4)_3$ | 26.3 | 46.1 | 25.4 | 25.6 |
| Monetite | $CaHPO_4$ | — | 2.7 | 15.8 | 15.4 |
| Brochantite | $Cu_4SO_4(OH)_6$ | — | — | 0.3 | 0.2 |
| Total | | 100 | 100 | 100 | 100 |

Data were normalized to 100% crystalline material.

ICP-OES

TABLE 2

Composition of powder samples after filtration.

| | SRCC 3 | SRCC 5 |
|---|---|---|
| Cu (ICP-OES, %) | 0.56 | 2.16 |

TABLE 3

Composition of filtered washing water from Powder 5.

| | 1 L washing |
|---|---|
| Calcium | 336 ± 5 ppm; ROR[a]: 95.0% |
| Copper | <0.1 ppm |

[a]ROR means rate of recovery of the measurement.

The XRD measurements show that a new crystalline calcium phase (monetite) has been formed in the inventive surface-reacted calcium carbonate. Furthermore, the inventive samples SRCC4 and SRCC5 show the presence of a copper mineral phase, namely, brochantite. The XRD measurements of SRCC3 did not reveal a significant copper phase. However, it could be confirmed by ICP-OES that SRCC3 contains copper.

For the analysis according to Table 3, 400 g of SRCC 5 filter cake (corresponding to 98 g solid) are dispersed with 1 litre deionised water and agitated (mechanical agitation, ca 300 rpm) for 30 minutes. The suspension is filtered, and the filtered solution is analysed to determine the amount of copper in 1 litre water. It can be gathered from Table 3 that only a very low amount of copper was leached into the water.

4. Slurries of Surface-reacted Calcium Carbonate Fillers and Paper Coatings

Examples 1 to 5 (E1 to E5) and Comparative Example 1 (CE1)

Slurries were prepared on a Pendraulik stirrer, by stirring mixtures of the compositions indicated in Table 4 below for 10 minutes at room temperature with 930 rpm.

TABLE 4

Composition of produced filler slurries.

| Example | SRCC | SRCC [parts by weight] | Water [parts by weight] | DA [parts by weight] | Solid content [wt.-%] | Brookfield viscosity [mPas] | pH | Conductivity [mS/cm] |
|---|---|---|---|---|---|---|---|---|
| CE1 | SRCC 11 | 100 | 100 | 0.7 | 46.7 | 348 | 9.2 | 1.7 |
| E1 | SRCC 1 | 100[a] | 465 | 0.7 | 17.7 | 992 | 7.5 | 1.2 |
| E2 | SRCC 3 | 100[b] | 405 | 0.7 | 19.5 | 1188 | 6.9 | 1.8 |
| E3 | SRCC 5 | 100[c] | 435 | 0.7 | 18.7 | 1098 | 6.6 | 2.0 |
| E4 | Powder 9 - mix of SRCC 3 and SRCC 11 washed (90:10 mixture) | 100 | 125 | 0.7 | 41.4 | 108.4 | 8.9 | 1.8 |
| E5 | Powder 10 - mix of SRCC 5 and SRCC 11 washed (90:10 mixture) | 100 | 125 | 0.7 | 41.6 | 138 | 8.7 | 1.9 |

[a] a 20.3 wt.-% filter cake from SRCC 1 was used.
[b] a 24.5 wt.-% filter cake from SRCC 3 was used.
[c] a 24.5 wt.-% filter cake from SRCC 5 was used.
DA = dispersing agent (100% sodium-neutralised polyacrylate, $M_w$ = 3 500 g/mol, pH = 8).

Coating colours containing 100 parts of the respective SRCC (w/w) and 6 parts (dry/dry) of Styronal D628 (BASF, Germany) were then prepared with slurries according to Examples 1 to 5 and Comparative Examples 1 and coated on superYUPO® foils from Fischer Papier AG, Switzerland (thickness 80 μm, size: 18×26 cm$^2$, 62 g/m$^2$, polypropylene). The composition of the coating colours and coating weights are summarized in Table 5 below.

TABLE 5

Coating colour preparation and coating weight.

| | | Coating colour composition | | | |
|---|---|---|---|---|---|
| Example | Slurry | SRCC [parts by weight] | Styronal D628 [parts, dry/dry] | Solid content [wt.-%] | Coating weight [g/m$^2$] |
| CE2 | CE1 (SRCC 11) | 100 | 6 | 40 | 12.4 |
| E6 | E1 (SRCC 1) | 100 | 6 | 18 | 4.4 |
| E7 | E2 (SRCC 3) | 100 | 6 | 18 | 4.6 |
| E8 | E3 (SRCC 5) | 100 | 6 | 18 | 8.1 |
| E9 | E4 (Powder 9 - mix of SRCC 3 and SRCC 11 washed (90:10 mixture)) | 100 | 6 | 40 | 14.5 |
| E10 | E5 (Powder 10 - mix of SRCC 5 and SRCC 11 washed (90:10 mixture)) | 100 | 6 | 40 | 13 |

Example 11—Antimicrobial Surface Activity of Paper Coatings

The antimicrobial activity of selected paper samples comprising a coating layer containing the surface-reacted calcium carbonate of the present invention as filler, which were prepared according to Examples 6 to 10 (E6 to E10) and Comparative Example 2 (CE2) was tested as described in the measurement method section "Antimicrobial surface activity test" above.

Tables 6 shows the cfu counts per test item and the calculated antimicrobial activity against *S. aureus* of the coated paper samples E6 to E10 as well as of comparative sample CE2. The term LOD in Table 6 refers to the limit of detection.

TABLE 6

Antimicrobial activity against *S. aureus* of surface coated paper samples.

| | cfu/test item | | | | Antimicrobial activity | |
|---|---|---|---|---|---|---|
| Test item | I | II | III | Average | R | LOD |
| untreated paper from CE2 (SRCC 11) (before incubation) | 2.9E+05 | 2.6E+05 | 2.5E+05 | 2.7E+05 | N/A | N/A |
| untreated paper from CE2 (SRCC 11) | 3.5E+03 | 1.6E+04 | 1.6E+04 | 1.2E+04 | 0.00 | 3.07 |
| Paper from E6 (SRCC 1) | 1.0E+01 | 1.0E+01 | 1.0E+01 | 1.0E+01 | 3.07 | 3.07 |
| Paper from E7 (SRCC 3) | 1.0E+01 | 1.0E+01 | 1.0E+01 | 1.0E+01 | 3.07 | 3.07 |
| Paper from E8 (SRCC 5) | 1.0E+01 | 1.0E+01 | 1.0E+01 | 1.0E+01 | 3.07 | 3.07 |
| Paper from E9 (Powder | 1.0E+01 | 1.0E+01 | 1.0E+01 | 1.0E+01 | 3.07 | 3.07 |

TABLE 6-continued

Antimicrobial activity against *S. aureus* of surface coated paper samples.

| Test item | cfu/test item | | | | Antimicrobial activity | |
|---|---|---|---|---|---|---|
| | I | II | III | Average | R | LOD |
| 9 - mix of SRCC 3 and SRCC 11 washed (90:10 mixture)) | | | | | | |
| Paper from E10 (Powder 10 - mix of SRCC 5 and SRCC 11 washed (90:10 mixture)) | 1.0E+01 | 1.0E+01 | 1.0E+01 | 1.0E+01 | 3.07 | 3.07 |

N/A: Not applicable

As can be gathered from the results compiled in Table 6 above, all paper samples with a coating layer comprising the inventive surface-reacted calcium carbonate show good antimicrobial activity.

The invention claimed is:

1. A surface-reacted calcium carbonate wherein the surface-reacted calcium carbonate is obtained by a process comprising the steps of:
   a) providing a calcium carbonate-comprising material, wherein the calcium carbonate-comprising material is a natural ground calcium carbonate;
   b) providing at least one $H_3O^+$ ion donor, wherein the at least one $H_3O+$ ion donor is phosphoric acid,
   c) providing at least one water-soluble metal cation source, wherein the at least one water-soluble metal cation source is selected from the group consisting of copper nitrate, copper sulphate, copper acetate, copper chloride, copper bromide, copper iodide, zinc nitrate, zinc sulphate, zinc acetate, zinc chloride, zinc bromide, zinc iodide, hydrates thereof, and mixtures thereof, and
   d) treating the calcium carbonate-comprising material of step a) with the at least one $H_3O^+$ ion donor of step b) and carbon dioxide in an aqueous medium to form an aqueous suspension of surface-reacted calcium carbonate, wherein in step d) the calcium carbonate-comprising material is treated with a solution comprising the at least one $H_3O+$ ion donor of step b) and the at least one water-soluble metal cation source of step c),
   wherein the carbon dioxide is formed in-situ by the $H_3O^+$ ion donor treatment of the calcium carbonate-comprising material and/or is supplied from an external source and the at least one water-soluble metal cation source of step c) is added during step d);
   wherein the surface-reacted calcium carbonate comprises the calcium carbonate-comprising material, at least one water-insoluble calcium salt other than calcium carbonate, and at least one water-insoluble metal cation salt incorporated into the internal structure of the surface-reacted calcium carbonate, and wherein the ratio of the at least one water-insoluble metal cation salt to calcium carbonate-comprising material is in the range of 0.00001:1 to 0.1:1 by weight.

2. The surface-reacted calcium carbonate of claim 1, wherein the calcium carbonate-comprising material is in the form of particles having a weight median particle size $d_{50}(wt)$ from 0.05 μm to 10 μm, and/or a weight top cut particle size $d_{98}(wt)$ from 0.15 μm to 55 μm.

3. The surface-reacted calcium carbonate of claim 2, wherein the weight median particle size $d_{50}(wt)$ is from 0.2 μm to 5.0 μm and/or the weight top cut particle size $d_{98}(wt)$ is from 1 μm to 40 μm.

4. The surface-reacted calcium carbonate of claim 1, wherein the molar ratio of the at least one $H_3O^+$ ion donor to the calcium carbonate-comprising material is from 0.01 to 4.

5. The surface-reacted calcium carbonate of claim 4, wherein the molar ratio is from 0.02 to 2.

6. The surface-reacted calcium carbonate of claim 1, wherein the at least one water-soluble metal cation source is provided in an amount from 0.01% wt. -% to 60 wt. -%, based on the total weight of the calcium carbonate-comprising material.

7. The surface-reacted calcium carbonate of claim 6, wherein the amount of the at least one water-soluble metal cation source is from 0.05 wt.-% to 50 wt.-%.

8. The surface-reacted calcium carbonate of claim 1, wherein in step d) the calcium carbonate-comprising material is treated with a first solution comprising a first part of the at least one $H_3O^+$ ion donor of step b), and subsequently, with a second solution comprising the remaining part of the at least one $H_3O^+$ ion donor of step b) and the at least one water-soluble metal cation source of step c).

9. The surface-reacted calcium carbonate of claim 1, wherein step d) is carried out at a temperature from 20° C. to 90° C.

10. The surface-reacted calcium carbonate of claim 1, wherein the process further comprises a step e) of separating the surface-reacted calcium carbonate from the aqueous suspension obtained in step d).

11. The surface-reacted calcium carbonate of claim 1, wherein the process further comprises a step f) of drying the surface-reacted calcium carbonate after step d) at a temperature in the range from 60° C. to 600° C.

12. The surface-reacted calcium carbonate of claim 11, wherein the drying is conducted until the moisture content of the surface-reacted calcium carbonate is from 0.01 wt.-% to 5 wt.-% based on the total weight of the dried surface-reacted calcium carbonate.

13. The surface-reacted calcium carbonate of claim 1, wherein the surface-reacted calcium carbonate has a specific surface area of from 15 m²/g to 200 m²/g measured using nitrogen and the BET method.

14. The surface-reacted calcium carbonate of claim 13, wherein the specific surface area is from 20 m²/g to 180 m²/g.

15. The surface-reacted calcium carbonate of claim 1, wherein the surface-reacted calcium carbonate has a volume determined median particle size $d_{50}(vol)$ from 1 μm to 75 μm and/or a volume determined top cut particle size $d_{98}(vol)$ from 2 μm to 150 μm.

16. The surface-reacted calcium carbonate of claim 15, wherein the volume determined median particle size $d_{50}$(vol) is from 2 μm to 50 μm and/or the volume determined top cut particle size $d_{98}$(vol) is from 4 μm to 100 μm.

17. The surface-reacted calcium carbonate of claim 1, wherein the surface-reacted calcium carbonate has an intra-particle intruded specific pore volume in the range from 0.1 cm$^3$/g to 2.3 cm$^3$/g calculated from mercury porosimetry measurement.

18. The surface-reacted calcium carbonate of claim 17, wherein the intra-particle intruded specific pore volume is from 0.2 cm$^2$/g to 2.0 cm$^3$/g.

19. The surface-reacted calcium carbonate of claim 1, wherein the surface-reacted calcium carbonate has an intra-particle pore size in a range of from 0.004 μm to 1.6 μm determined from mercury porosimetry measurement.

20. The surface-reacted calcium carbonate of claim 19, wherein the intra-particle pore size is from 0.005 μm to 1.3 μm.

21. The surface-reacted calcium carbonate of claim 1, wherein the ratio of the at least one water-insoluble metal cation salt to calcium carbonate-comprising material is in the range of 0.001 to 0.01 by weight.

22. A composition comprising a surface-reacted calcium carbonate according to claim 1, the composition further comprising an additional surface-reacted calcium carbonate, wherein the additional surface-reacted calcium carbonate is a reaction product of natural ground calcium carbonate or precipitated calcium carbonate with carbon dioxide and at least one $H_3O^+$ ion donor, wherein the carbon dioxide is formed in-situ by the $H_3O^+$ ion donor treatment and/or is supplied from an external source.

23. An article comprising a surface-reacted calcium carbonate according to claim 1, wherein the article is selected from the group consisting of paper products, engineered wood products, plasterboard products, polymer products, hygiene products, medical products, healthcare products, filter products, woven materials, nonwoven materials, geo-textile products, agriculture products, horticulture products, clothing, footwear products, baggage products, household products, industrial products, packaging products, building products, and construction products.

24. The surface-reacted calcium carbonate of claim 1, wherein the natural ground calcium carbonate is selected from the group consisting of marble, chalk, dolomite, limestone, and mixtures thereof.

* * * * *